United States Patent [19]

Berger et al.

[11] Patent Number: 5,202,318

[45] Date of Patent: Apr. 13, 1993

[54] TRICYCLIC COMPOUNDS ACTING AT SEROTONIN RECEPTOR SUBTYPES

[75] Inventors: Jacob Berger, Los Altos Hills; Robin D. Clark, Palo Alto; Richard M. Eglen, Mountain View; William L. Smith, Sunnyvale; Klaus K. Weinhardt, San Francisco, all of Calif.

[73] Assignee: Syntex (U.S.A.) Inc., Palo Alto, Calif.

[21] Appl. No.: 708,260

[22] Filed: May 28, 1991

Related U.S. Application Data

[63] Continuation-in-part of Ser. No. 523,090, May 14, 1990, abandoned.

[51] Int. Cl.⁵ .................. C07D 471/08; A61K 31/55; A61K 31/455
[52] U.S. Cl. .................................. 514/211; 514/296; 514/872; 540/584; 546/99; 546/100
[58] Field of Search ................. 546/99, 100; 514/211, 514/296; 540/520

[56] References Cited

U.S. PATENT DOCUMENTS

| | | | |
|---|---|---|---|
| 3,940,398 | 2/1976 | Wade et al. | 424/251 |
| 4,007,191 | 2/1977 | Wade et al. | 546/99 |
| 4,146,720 | 3/1979 | Roldan et al. | 546/100 |
| 4,204,063 | 5/1980 | Brana et al. | 546/100 |
| 5,039,681 | 8/1991 | Sugimoto et al. | 546/99 |

FOREIGN PATENT DOCUMENTS

| | | |
|---|---|---|
| 0093488 | 11/1983 | European Pat. Off. |
| 0200444 | 11/1986 | European Pat. Off. |
| 0243841 | 11/1987 | European Pat. Off. |
| 0247266 | 12/1987 | European Pat. Off. |
| 0269355 | 6/1988 | European Pat. Off. |
| 0315390 | 5/1989 | European Pat. Off. |
| 0404737 | 12/1990 | European Pat. Off. |
| 0436157 | 7/1991 | European Pat. Off. |

OTHER PUBLICATIONS

Reynolds, J. C. Prokinetic Agents: A Key in the Future of Gastroenterology *Gastroenterology Clinics of North America* 1989; 18(2): 437–457.

Drugs Acting on 5-Hydroxytryptamine Receptors *The Lancet* Sep. 23, 1989; 717–719.

Peatfield, R. Drugs and the Treatment of Migraine *Trends Pharmacol. Sci.* 1988; 9: 141–145.

Fozard, J. R. 5-HT: The Enigma Variations *Trends Pharmacol. Sci.* 1987; 8: 501–506.

Sato et al. New and Convenient Synthesis of 2-Substituted 2,3-Dihydro-1H-Benz[de]isoquinolin-1-Ones *Bulletin of the Chemical Society of Japan* 1988; 61(5): 2238–2240.

Alexiou et al. Nucleophilic Displacement of the Nitro Group in 2- and 4-Nitronaphthalic-1,8-Anhydrides and Their Derivatives *Tetrahedron Letters* 1981; 22(19): 2303–2306.

*Primary Examiner*—Mark L. Berch
*Attorney, Agent, or Firm*—Wayne W. Montgomery; Derek P. Freyberg; Tom M. Moran

[57] ABSTRACT

Compounds of Formula I:

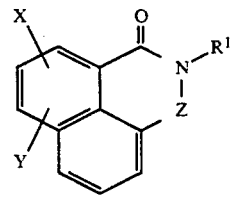

in which
Z is $CH_2$ or $C=O$;
X and Y are independently selected from hydrogen, halogen, hydroxy, lower alkoxy, lower alkyl, nitro, amino, aminocarbonyl, (lower alkyl)amino, di(lower alkyl)amino and (lower alkanoyl)amino; and $R^1$ is a group selected from Formulae (a), (b), (c) (d) and (e):

(Abstract continued on next page.)

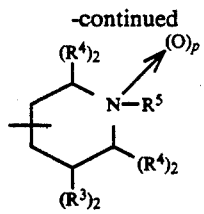

in which
p is 0 or 1;
n is 1, 2 or 3;
$R^2$ is hydrogen, lower alkyl, $C_{3-8}$ cycloalkyl, $C_{3-8}$ cycloalkyl-$C_{1-2}$ alkyl, or a group $R^6$-$C_{1-2}$ alkyl in which $R^6$ is thienyl, pyrrolyl or furyl optionally substituted by one or two substituents selected from lower alkyl, lower alkoxy, trifluoromethyl or halogen, or is phenyl optionally substituted by one or two substituents selected from $C_{1-4}$ alkoxy, trifluoromethyl, halogen, nitro, carboxy, esterified carboxy, and $C_{1-4}$ alkyl optionally further substituted by hydroxy, $C_{1-4}$ alkoxy, carboxy, esterified carboxy or in vivo hydrolyzable acyloxy;
each $R^3$ is independently selected from hydrogen, hydroxy, alkyl and alkoxy;
each $R^4$ is independently hydrogen or alkyl; and
$R^5$ is hydrogen, lower alkyl, $C_{3-8}$ cycloalkyl, $C_{3-8}$ cycloalkyl-$C_{1-2}$ alkyl, alkenyl, alkynyl or a group $R^7$-$C_{1-3}$ alkyl in which $R^7$ is phenyl or phenoxy optionally substituted by one or two substituents selected from $C_{1-4}$ alkoxy, trifluoromethyl, halogen, nitro, carboxy, esterified carboxy, and $C_{1-4}$ alkyl optionally further substituted by hydroxy, $C_{1-4}$ alkoxy, carboxy, esterified carboxy or in vivo hydrolyzable acyloxy; and the pharmaceutically acceptable salts, individual isomers, mixtures of isomers, processes for preparation, compositions, and methods of use thereof.

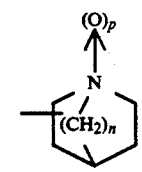  (a)

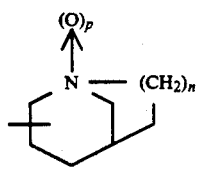  (b)

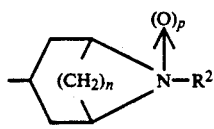  (c)

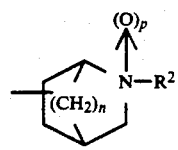  (d)

52 Claims, No Drawings

TRICYCLIC COMPOUNDS ACTING AT SEROTONIN RECEPTOR SUBTYPES

This application is a continuation-in-part of copending application, Ser. No. 07/523,090, filed May 14, 1990 and now abandoned.

FIELD OF THE INVENTION

This invention relates to azabicyclobenzisoquinolines which interact at serotonin receptor subtypes.

BACKGROUND OF THE INVENTION

Serotonin, a neurotransmitter with mixed and complex pharmacological characteristics, was first discovered in 1948 and subsequently has been the subject of substantial research. Serotonin, also referred to as 5-hydroxytryptamine (5-HT), acts both centrally and peripherally on discrete 5-HT receptors. 5-HT Receptors are presently delineated into three major subclassifications—$5\text{-}HT_1$, $5\text{-}HT_2$ and $5\text{-}HT_3$- each of which may also be heterogeneous.

Molecules which selectively interact with the serotonergic receptor subtypes represent a family of drugs with a diversity of therapeutic applications. For example, $5\text{-}HT_1$ receptor agonists are clinically indicated for anxiety, hypertension and migraine. Selective $5\text{-}HT_2$ receptor antagonists are indicated as anxiolytics, anti-depressants, anti-hypertensives and appetite stimulants (see 5-HT: The Enigma Variations. J. R. Fozard Trends. Pharmacol. Sci. 1987, 8: 501).

$5\text{-}HT_3$ receptor antagonists are known for their potent antiemetic properties, particularly against emesis induced by cancer chemotherapy and radiotherapy, and for their gastrokinetic activity (see respectively, Drugs Acting on 5-Hydroxytryptamine Receptors The Lancet Sep. 23, 1989 and references cited therein and Prokinetic Agents: A Key in the Future of Gastroenterology. Reynolds R.C. Gastroenterology Clinics of North America 1989, 18, 437–457). In addition, $5\text{-}HT_3$ receptor antagonists may be useful in treating CNS diseases involving cognitive dysfunctions, anxiety, dependency disorders and schizophrenia (see article from The Lancet previously cited) and may also be of value in the control of pain, particularly migraine (see Drugs and the Treatment of Migraine. Peatfield R. Trends. Pharmacol. Sci. 1988, 9, 141).

The disclosures of these and other documents referred to throughout this application, e.g., in the Pharmacology section of the Detailed Description of the Invention, are incorporated herein by reference.

SUMMARY OF THE INVENTION

The first aspect of this invention is the compounds of Formula I:

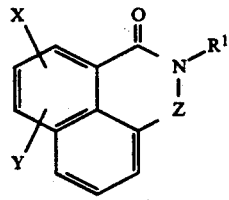

in which
Z is $CH_2$ or $C=O$;
X and Y are independently selected from hydrogen, halogen, hydroxy, lower alkoxy, lower alkyl, nitro, amino, aminocarbonyl, (lower alkyl)amino, di(lower alkyl)amino and (lower alkanoyl)amino; and
$R^1$ is a group selected from Formulae (a), (b), (c), (d) and (e):

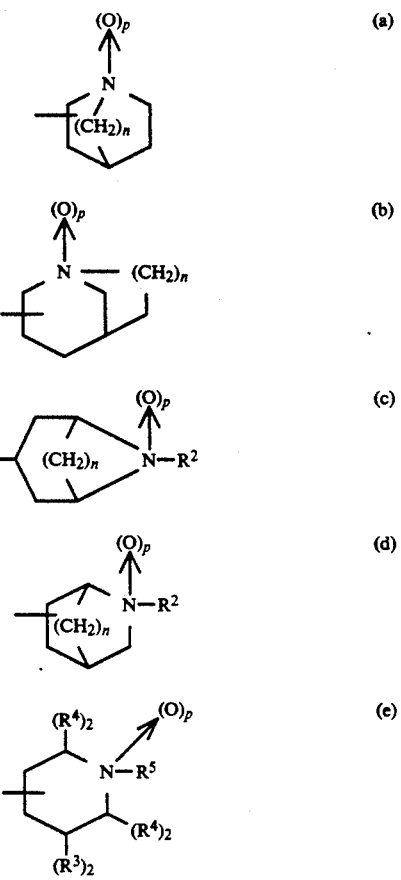

in which
p is 0 or 1;
n is 1, 2 or 3;
$R^2$ is hydrogen, lower alkyl, $C_{3\text{-}8}$ cycloalkyl, $C_{3\text{-}8}$ cycloalkyl-$C_{1\text{-}2}$ alkyl, or a group $R^6\text{-}C_{1\text{-}2}$ alkyl in which $R^6$ is thienyl, pyrrolyl or furyl optionally substituted by one or two substituents selected from lower alkyl, lower alkoxy, trifluoromethyl or halogen, or is phenyl optionally substituted by one or two substituents selected from $C_{1\text{-}4}$ alkoxy, trifluoromethyl, halogen, nitro, carboxy, esterified carboxy, and $C_{1\text{-}4}$ alkyl optionally further substituted by hydroxy, $C_{1\text{-}4}$ alkoxy, carboxy, esterified carboxy or in vivo hydrolyzable acyloxy;
each $R^3$ is independently selected from hydrogen, hydroxy, alkyl and alkoxy;
each $R^4$ is independently hydrogen or alkyl; and
$R^5$ is hydrogen, lower alkyl, $C_{3\text{-}8}$ cycloalkyl, $C_{3\text{-}8}$ cycloalkyl-$C_{1\text{-}2}$ alkyl, alkenyl, alkynyl or a group $R^7\text{-}C_{1\text{-}3}$ alkyl in which $R^7$ is phenyl or phenoxy optionally substituted by one or two substituents selected from $C_{1\text{-}4}$ alkoxy, trifluoromethyl, halogen, nitro, carboxy, esterified carboxy, and $C_{1\text{-}4}$ alkyl optionally further substituted by hydroxy, $C_{1\text{-}4}$ alkoxy, carboxy, esterified carboxy or in vivo hydrolyzable acyloxy; and the pharmaceutically acceptable salts, individual isomers, and mixtures of isomers thereof.

A second aspect of this invention is a pharmaceutical composition which contains a compound of Formula I in admixture with one or more suitable excipients.

A third aspect of this invention is a method for the treating diseases involving emesis, gastrointestinal disorders, CNS disorders, cardiovascular disorders or pain by administering a therapeutically effective amount of a compound of Formula I to a subject in need thereof.

A fourth aspect of this invention is the compounds of Formula IIIA and IIIB which are useful intermediates for preparing compounds of Formula I:

IIIA

IIIB in which $R^8$ and $R^9$ are independently hydroxy, alkoxy or halogen, and X, Y, Z and R are as defined for Formula I.

A fifth aspect of this invention is the processes for preparing compounds of Formula I and is set forth in "Detailed Description of the Invention".

DETAILED DESCRIPTION OF THE INVENTION

Definitions

Unless otherwise stated, the following terms used in the specification and claims have the meanings given below:

"Alkyl" means a straight, branched, or cyclic saturated hydrocarbon radical having from one to the number of carbon atoms designated. For example $C_{1-4}$ alkyl is alkyl having at least one but no more than seven carbon atoms, e.g., methyl, ethyl, i-propyl, n-propyl, n-butyl, cyclopropylmethyl, pentyl, cyclohexyl, heptyl and the like.

"Alkoxy" means the radical —OR wherein R is alkyl having from one to the number of carbon atoms designated, e.g., $C_{1-7}$ alkoxy includes methoxy, ethoxy, i-propoxy, n-propoxy, n-butoxy, pentoxy, hexoxy and the like.

"Alkanoyl" means the radical —C(O)R wherein R is alkyl having from one to the number of carbon atoms designated, e.g., $C_{1-7}$ alkanoyl includes ethanoyl, propanoyl, i-butanoyl, n-butanoyl, pentanoyl, hexanoyl and the like.

"Alkenyl" means a straight, branched, or cyclic unsaturated hydrocarbon radical containing from 2 to 10 carbon atoms with at least one double bond between two carbon atoms, e.g., ethenyl, n-prop-1-enyl, n-prop-2enyl, i-propenyl, n-butenyl, cyclopropenylmethyl, pentenyl, cyclohexenyl and the like.

"Alkynyl" means a straight or branched unsaturated hydrocarbon radical containing from 2 to 8 carbon atoms with at least one triple bond between two carbon atoms, e.g., ethynyl, prop-1-ynyl, prop-2-ynyl, butynyl, pentynyl and the like.

"Lower" modifies alkyl, alkoxy and alkanoyl and refers to those alkyl radicals or R groups in alkoxy and alkanoyl radicals containing 1 to 6 carbon atoms.

"Halogen" means fluorine, chlorine, bromine, or iodine.

"Esterified carboxy" means the ester group —COOR wherein R is $C_{1-8}$ alkyl.

"In vivo hydrolyzable acyloxy" means a group —OC(O)R, wherein R is $C_{1-8}$ alkyl, capable of undergoing enzymatic hydrolysis within a living organism.

"Leaving group" has the meaning conventionally associated with it in synthetic organic chemistry, i.e., an atom or group displaceable under alkylating conditions, and includes halogen and alkane- or arenesulfonyloxy such as mesyloxy, ethanesulfonyloxy, benzenesulfonyloxy, tosyloxy and the like.

"Animal" includes humans, non-human mammals, e.g., dogs, cats, rabbits, cattle, horses, sheep, goats, swine, and deer, and non-mammals, e.g., birds and the like.

"Cytotoxic agents" include platinum anti-cancer agents, e.g., cisplatin (cis-diamminedichloroplatinum), as well as non-platinum anti-cancer drugs, e.g., cyclophosphamide (cytoxin), vincristrine (leurocristine), procarbazine (N-(1-methylethyl)-4-[(2-methylhydrazino)-methyl]benzamide), methotrexate, fluorouracil, mechlorethamine hydrochloride (2-chloro-N-(2-chloroethyl)-N-methylethanamine hydrochloride), doxorubicin, adriamycin, dactinomycin (actinomycin-D) cytarabine, carmustine, dacarbazine, and others listed at page 1143 of the Journal of Clinical Oncology 1989, 7(8), 1143.

"Disease" specifically includes any unhealthy condition of an animal or part thereof and includes an unhealthy condition which may be caused by, or incident to, medical or veterinary therapy applied to that animal, i.e., the "side effects" of such therapy. Thus, "disease" here includes the emesis caused by therapy with agents having emetogenic side effects, in particular by therapy for cancer, such as chemotherapy with cytotoxic agents and radiotherapy.

"Emesis", for the purposes of this application, will have a meaning that is broader than the normal, dictionary definition and includes not only vomiting, but also nausea and retching.

"Optional" or "optionally" means that the subsequently described event or circumstance may or may not occur, and that the description includes instances where the event or circumstance occurs and instances in which it does not. For example, "optional bond" means that the bond may or may not be present and that the description includes both single bonds and double bonds; "optionally converting a compound of Formula I to a corresponding pharmaceutically acceptable salt" means that the conversion may or may not be carried out in order for the process described to fall within the invention, and the invention includes those processes wherein the compound of Formula I is converted to the salt and those processes in which it is not.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Therapeutically effective amount" means that amount which, when administered to an animal for treating a disease, is sufficient to effect such treatment for the disease.

"Treating" or "treatment" of a disease includes: (1) preventing the disease from occurring in an animal which may be predisposed to the disease but does not yet experience or display symptoms of the disease, (2) inhibiting the disease, i.e., arresting its development, or (3) relieving the disease, i.e., causing regression of the disease.

"Isomerism" is the phenomenon wherein compounds have identical molecular formulae but differ in the nature or sequence of bonding of their atoms or in the arrangement of their atoms in space. Isomers that differ in the nature or sequence of bonding of their atoms are termed "constitutional isomers". Isomers that differ only in the arrangement of their atoms in space are termed "stereoisomers". Stereoisomers that are not mirror images of one another are termed "diastereomers" and stereoisomers that are the nonsuperimposable mirror images of one another are termed "enantiomers" or sometimes "optical isomers".

Stereoisomers that are superimposable upon their mirror images are termed "achiral" and those not superimposable are termed "chiral". A carbon atom bonded to four different atoms or groups is termed a "chiral center" or alternatively an "asymmetric carbon". A carbon atom bonded to two atoms or groups the interchange of which produces a nonidentical compound is termed a "stereogenic atom". A chiral compound has two enantiomeric forms of opposite chirality. A chiral compound may exist as any individual enantiomer or as a mixture of enantiomers. A mixture containing equal proportions of the enantiomers is termed a "racemic mixture" or "racemate". A chiral compound that has more than one chiral center has $2^{n-1}$ enantiomeric pairs, where n is the number of asymmetric carbons. An achiral diastereomer having chiral centers is termed "meso". An achiral diastereomer without a chiral center is termed a "geometric isomer".

A chiral stereoisomer is characterized by the absolute configuration of its chiral center(s). Absolute configuration refers to the arrangement in space of atoms or groups attached to a chiral center. The atoms or groups attached to the chiral center under consideration are ranked in accordance with the Sequence Rule of Cahn and Prelog and the center is specified as either R or S. A chiral stereoisomer is also characterized in terms of its optical activity, i.e., the manner in which the molecule rotates the plane of polarized light. An optically active molecule is described as dextrorotatory or levorotatory and specified as the (d)- or (l)-isomer, or the (+)- or (−)-isomer, respectively. Racemic mixtures are described as the (RS)- or (±)-mixture thereof.

An achiral stereoisomer is described by the absolute configuration of its stereogenic atoms. The geometric isomers of bicyclo[X.Y.Z]alkanes, in which $X \geq Y \geq Z \geq 0$, are described by specifying each of the senior substituents at the stereogenic positions on the ring formed by the X and Y bridges as exo if the substituent and the Z bridge are on the same side of the ring and as endo if on opposite sides.

The geometric isomers of cycloalkanes in which two stereogenic positions on the ring exist are described by specifying as cis or trans when senior substituents are on the same or opposite sides, respectively, of the ring. The geometric isomers of cycloalkanes in which three or more stereogenic positions exist in the ring are described by specifying the configuration of the senior substituents at the stereogenic positions in terms relative to the configuration of the senior substituent bonded to the reference center, i.e., the lowest-numbered stereogenic position on the ring. The side of the ring on which the senior substituent lies at the reference center is designated the α-side and senior substituents at the remaining stereogenic positions are specified as α or β depending on whether the substituent is on the α or the opposing side.

The geometric isomers of alkenes are described as Z and E when senior substituents are on the same or opposite sides, respectively, of the double bond.

Conventions for stereochemical nomenclature, methods for the determination of stereochemistry and the separation of stereoisomers are well-known in the art (see discussion in Chapter 4 of Advanced Organic Chemistry March, 1985, 3rd edition, Jerry, John Wiley and Sons, New York).

Certain compounds of Formula I and intermediates in the synthesis thereof can exist as stereoisomers. For example, certain compounds possess chiral centers at the ring carbon which is bonded to the amide nitrogen and, when $R^1$ is Formula (e), at the 2, 3, and/or 6 positions of the piperidinyl group and can exist as the (R)—or (S)-isomers thereof. In addition, certain compounds in which $R^1$ is Formula (a), (b), (c) or (d) can exist as the (endo)- or (exo)-isomers and certain compounds in which $R^1$ is Formula (e) can exist as any of various geometric isomers in the cis and trans or α and β forms. Lastly, certain compounds in which $R^1$ is Formula (e) and $R^3$ is alkenyl can exist as (Z)- and (E)-isomers.

It is to be understood that when referring by structure to a compound of Formula I or an intermediate in the synthesis thereof, a straight line depicting a covalent bond to the ring of an azacycloalkyl group represented by Formula (a), (b), (c), (d) or (e) represents the diastereomeric, including geometric, and enantiomeric forms of the compound or the mixtures, racemic or otherwise, thereof. Unless indicated otherwise, the description or naming of a particular compound in the specification and claims is intended to include the individual stereoisomers and mixtures thereof, e.g., individual enantiomers and mixtures of isomers, racemic or otherwise.

Certain R¹ substituents described in this application are of particular interest and are therefore defined specifically as follows:

(1) Formula (c) where n is 2 and p is 0 having the specific formula

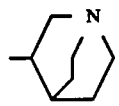

is referred to as 1-azabicyclo[2.2.2]oct-3-yl;

(2) Formula (b) where n is 2 and p is 0 having the specific formula

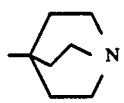

is referred to as 1-azabicyclo[2.2.2]oct-4-yl;

(3) Formula (e) wherein each R³ and R⁴ is hydrogen, R⁵ is methyl and p is 0 having the specific formula

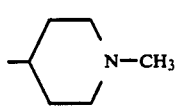

is referred to as 1-methylpiperidin-4-yl.

(4) Formula (a) where n is 3, p is 0 and R² is methyl having the specific formula

is referred to as (endo)-9-methyl-9-azabicyclo[3.3.1.]-non-3-yl;

(5) Formula (a) where n is 3, p is 0 and R² is methyl having the specific formula

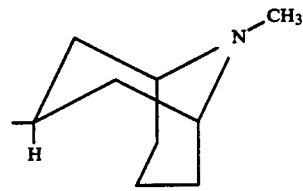

is referred to as (exo)-9-methyl-9-azabicyclo[3.3.1]non-3-yl;

(6) Formula (a) where n is 2, p is 0 and R² is methyl having the specific formula

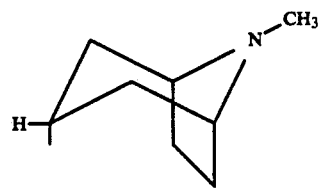

is referred to as (endo)-8-methyl-8-azabicyclo[3.2.1]-non-3-yl;

(7) Formula (a) where n is 2, p is 0 and R² is methyl having the specific formula

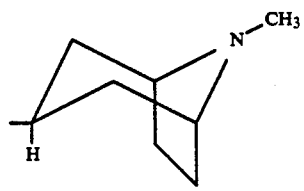

is referred to as (exo)-8-methyl-8-azabicyclo[3.2.1.]non-3-yl;

(8) Formula (c) wherein n is 2 and p is 0 having the specific formula

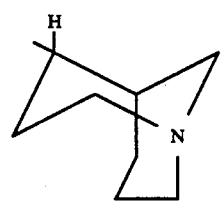

is referred to as (endo)-1-azabicyclo[3.3.1]non-4-yl;

(9) Formula (b) wherein n is 2 and p is 0 having the specific formula

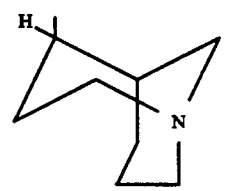

is referred to as (exo)-1-azabicyclo[3.3.1]non-4-yl; and

The compounds of Formula I are named in accordance with acceptable nomenclature rules generally consistent with "Chemical Abstracts", For example, the compound of Formula I in which both X and Y are hydrogen, Z is C=O and R¹ is 1-azabicyclo-[2.2.2]oct-3-yl

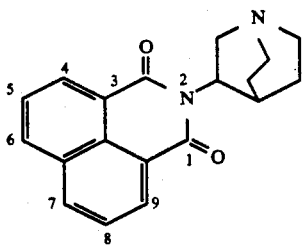

is named 2-(1-azabicyclo[2.2.2]oct-3-dihydro-1H-benz-[de]isoquinoline-1,3-dione.

Although deviating from accepted rules of nomenclature, but to be consistent with the general Formula I, the compound of Formula I in which both X and Y are hydrogen, Z is $CH_2$ and $R^1$ is 1-azabicyclo-[2.2.2]oct-3-yl

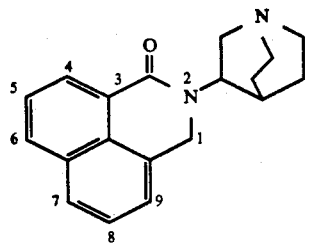

is named 2-(1-azabicyclo[2.2.2.]oct-3-yl)-2,3-dihydro-1H-benz[de]isoquinoline-3-one.

PRESENTLY PREFERRED EMBODIMENTS

While the broadest definition of this invention is set forth in the Summary of the Invention, certain compounds of Formulae I and III are preferred. For example, preferred compounds of Formula I are those in which X and Y are independently selected from hydrogen, halogen, nitro, aminocarbonyl and amino, and $R^2$ is lower alkyl, particularly those compounds in which $R^2$ is methyl and $R^1$ is one of the following groups: 1-azabicyclo[2.2.2]oct-3-yl; 1-azabicyclo[2.2.2]oct-4-yl; 1-methylpiperidin-4-yl; endo-9-methyl-9-azabicyclo[3.3.1]non-3-yl; exo-9-methyl-9-azabicyclo[3.3.1]non-3-yl; endo-8-methyl-8-azabicyclo[3.2.1]oct-3-yl; exo-8-methyl-8-azabicyclo[3.2.1]oct-3-yl; endo-1-azabicyclo[3.3.I]non-4-yl; or exo-1-azabicyclo[3.3.1]non-4-yl.

Of most interest are compounds of Formula I in which X and Y are independently selected from hydrogen, halogen, nitro, aminocarbonyl or amino, and $R^2$ is lower alkyl and $R^1$ is 1-azabicyclo[2.2.2]oct-3-yl, in particular the S-isomers, thereof. Representative compounds are made by following the procedures set out in Examples 1, 2, 3, 4, 5 and 6.

It is understood that these compounds of Formula I of special interest are particularly useful in the pharmaceutical compositions and methods of treatment of this invention.

Utility

Compounds of Formula I exhibit utility in treating a broad range of diseases in animals, particularly humans. Examples of diseases that may be treated using the compounds of Formula I include emesis, gastrointestinal disorders, central nervous system (CNS) disorders, cardiovascular disorders or pain.

Compounds of Formula I are useful in the prevention and treatment of emesis. Causes of such emesis include surgical anesthesia, psychological stress, pregnancy, certain disease states, radiotherapy, radiation poisoning and toxic substances. Disease states which are known to induce emesis include conditions such as gut obstruction, raised intracranial pressure, acute myocardial infarction, migraine headaches and adrenal crisis. Toxic substances which induce emesis include toxins in the form of abnormal metabolites or abnormal accumulation of natural occurring substances associated with such conditions as hepatic coma, renal failure, diabetic ketoacidosis, hyperthyroid crisis, both hypo- and hyperparathyroidism and Addison's disease. Emesis may also be caused by ingested toxins, e.g., enterotoxins in staphylococcus-contaminated foods, or by drugs administered for therapeutic purposes, e.g., digitalis, emetine and chemotherapeutic agents.

Compounds of Formula 1 are of particular value in treating (especially preventing) the emesis induced by radiation poisoning, treatment for cancer with radiotherapy or chemotherapy with cytotoxic agents or drug therapy in general wherein a significant side effect is emesis, e.g., amphotericin B in treating immunosuppressed patients, zidovudine (AZT) in the treatment of AIDS and interleukin in treating cancer.

Compounds of Formula I are useful as prokinetic agents in the treatment of gastrointestinal diseases, i.e., diseases of the stomach, esophagus and of both the large and small intestines. Examples of specific diseases include, but are not limited to, dyspepsia (e.g., non-ulcer dyspepsia), gastric stasis, peptic ulcer, reflux esophagitis, flatulence, bile reflux gastritis, pseudo-obstruction syndrome, irritable colon syndrome (which may result in chronic constipation and diarrhea), diverticular disease, biliary dysmotility (which may result in sphincter of Oddi dysfunction and "sludge" or microscopic crystals in the gall bladder), gastroparesis (e.g., diabetic, postsurgical or idiopathic), irritable bowel syndrome amd retarded gastric emptying. The compounds of Formula I are also useful as short-term prokinetics to facilitate diagnostic radiology and intestinal intubation. In addition, the compounds are useful for treating diarrhea, particularly diarrhea induced by cholera and carcinoid syndrome.

Compounds of Formula I are useful in treating diseases of the central nervous system. Categories of such diseases include cognitive disorders, psychoses, obsessive/compulsive and anxiety/depression behavior. Cognitive disorders include attentional or memory deficit, dementia states (including senile dementia of the Alzheimer's type and aging), cerebral vascular deficiency and Parkinson's disease. Psychoses that are treatable using the compounds of Formula I include paranoia, schizophrenia and autism. Obsessive/compulsive behavior treatable using the compounds of Formula I include eating disorders, e.g., bulimia, a condition in which an abnormal and constant craving for food is present. Representative, treatable anxiety/depressive states include anticipatory anxiety (e.g., prior to surgery, dental work, etc.), depression, mania, seasonal affective disorder (SAD), and the convulsions and anxiety caused by withdrawal from addictive substances such as opiates, benzodiazapines, nicotine, alcohol, cocaine and other drugs of abuse.

Compounds of Formula I are useful in the treatment of cardiovascular diseases. Such diseases include arrhythmias and hypertension.

It is thought that 5-HT$_3$ antagonists prevent certain adverse nervous transmissions and/or prevent vasodilation and are therefore of value for reducing perceived levels of pain. Compounds of Formula I are, therefore, useful in treating pain such as that associated with cluster headaches, migraines, trigeminal neuralgia and visceral pain (e.g., that caused by abnormal distension of hollow visceral organs).

In summary, an aspect of this invention is a method for treating an animal, particularly a human, exhibiting a disease involving emesis, a gastrointestinal disorder, a CNS disorders, a cardiovascular disorder or pain by administering a therapeutically effective amount of a compound of Formula I to such animal.

Pharmacology

Serotonin receptor binding affinity is measured at 5-HT$_3$ receptors in membranes prepared from the cerebral cortex of rat brains, an accepted in vitro assay (e.g., see Kilpatrick, G. J.; Jones, B. J.; Tyers, M. B. Nature 1987, 330, 24–31). The 5-HT$_3$ receptor binding assay is described in Example 15. The compounds of Formula I exhibit affinity for the 5-HT$_3$ receptor in this assay.

Anti-emetic activity is determined by measuring reduction of cisplatin-induced emesis in ferrets, an accepted assay (e.g., see Costall, B.; Domeney, A. M.; Naylor, R. J.; Tattersall, F. D. Neuropharmacology 1986, 25(8), 959–961; Miner, W. D.; Sanger G. J. Brit. J. Pharmacol. 1986, 88, 497–499). The ferret, anti-emetic assay is described in Example 16.

Anti-emetic activity is also determined by measuring reduction of cisplatin-induced emesis in dogs, an accepted assay (e.g., see Smith, W. L.; Alphin, R. S.; Jackson, C. B.; Sancilio, L. F. J. Pharm. Pharmacol. 1989, 41, 101–105; Gylys, J. A. Res. Commun. Chem. Pathol. Pharmacol. 1979, 23(1), 61–68). The dog, anti-emetic assay is described in Example 17.

Prokinetic activity is determined by measuring the rate of gastric emptying after oral administration of test meal to rats, an accepted in vivo assay (e.g., see Dropleman, D.; Gregory, R.; Alphin, R. S. J. Pharmacol. Methods 1980, 4(3), 227–30). The prokinetic assay is described in Example 18.

Anxiolytic activity is determined by the art-recognized Crawley and Goodwin two-compartment exploratory model (e.g., see Kilfoil, T.; Michel, A.; Montgomery, D.; Whiting, R. L. Neuropharmacology 1989, 28(9), 901–905). In brief, the method involves determining whether a compound reduces the natural anxiety of mice in a novel, brightly lighted area. The anxiolytic behavior assay is described in Example 18.

Anxiolytic activity during withdrawal from drugs of abuse is determined by the mouse, withdrawal anxiety test, an accepted assay (e.g., see Carboni, E.; Acquas, E.; Leone, P.; Perezzani, L.; Di Chiara, G. Eur. J. Pharmacol 1988, 151, 159–160). This procedure utilizes the exploratory model described above to test for anxiolytic activity after chronic administration and subsequent abrupt cessation of ethanol, cocaine diazepam or nicotine treatments. The withdrawal anxiety assay is described in Example 20.

Cognition enhancing activity is determined by the mouse, habituation/cognitive enhancement test (e.g., see Barnes, J. M.; Costall, B.; Kelly, M. E.; Naylor, F. J.; Onaivi, E. S.; Tomkins, D. M.; Tyers, M. B. Br. J. Pharmacol. 1989, 98, 693p). This procedure utilizes the exploratory model described above to test for improvements in the impaired cognitive performance of aged mice. The cognitive enhancement assay is described in Example 21.

Administration and Pharmaceutical Composition

In general, compounds of Formula I will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. Therapeutically effective amounts of compounds of Formula I may range from approximately 1.0 nanogram per Kg (ng/Kg) body weight per day to 1.0 mg/Kg body weight per day. Preferably the amount will be approximately 10 ng/Kg/day to 0.1 mg/Kg/day. Therefore, a therapeutically effective amount for a 70 Kg human may range from 70 ng/day to 70 mg/day, preferably 700 ng/day to 7.0 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

In general, compounds of Formula I will be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the compound of Formula I in aerosol form. Inert gases suitable for this purpose are nitrogen, carbon dioxide, nitrous oxide, etc. Other suitable pharmaceutical carriers and their formulations are described in A. R. Alfonso Remington's Pharmaceutical Sciences 1985, 17th ed. Easton, Pa.: Mack Publishing Company.

The amount of a compound of Formula I in the composition may vary widely depending upon the type of formulation, size of a unit dosage, kind of excipients and other factors known to those of skill in the art of pharmaceutical sciences. In general, the final composition will comprise from 0.000001% w to 10.0% w of the compound of Formula I, preferably 0.00001%w to 1.0

% w, with the remainder being the excipient or excipients.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 7.

PROCESSES FOR PREPARING COMPOUNDS OF THE INVENTION

Compounds of Formula I are prepared by the reaction sequences shown below in Scheme I.

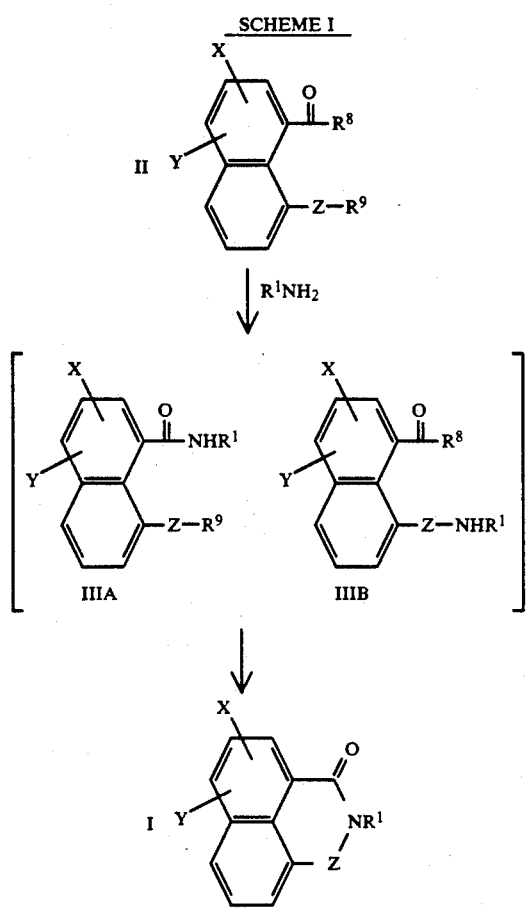

in which $R^8$ and $R^9$ are independently hydroxy, alkoxy, or halogen or are together oxa, and X, Y, Z and $R^1$ are as defined in the Summary of the Invention, with the processes applying particularly well to the presently preferred embodiments.

SCHEME I

Compounds of Formula I are conveniently prepared by converting a compound of Formula II to a substituted amide of Formula I. The conversion is carried out by reacting a compound of Formula II with a substituted amine of the formula $R^1NH_2$ at 80° to 200° C., ambient pressure, and in a suitable solvent (e.g., hydrocarbons, aromatic hydrocarbons such as xylene, toluene, tetralin or biphenyl, alcohols such as ethanol, n-butanol or isoamylalcohol, and ethers such as 1,4-dioxane, pentylether, diglyme (2-methoxyethyl ether) or diphenylether). The reaction mixture is heated at reflux temperature until no further reaction occurs (3 to 6 hours) or until the intermediates of Formulae IIIA and IIIB are formed. The intermediates of Formulae IIIA and IIIB can be isolated and then converted to a compound of Formula I in a separate reaction. The conversion of a compound of Formula II to a compound of Formula I is described in Examples 1, 2 and 3. The conversion of a compound of Formula II to intermediates of Formula IIIA and IIIB followed by the conversion to a compound of Formula I in a separate reaction is described in Example 4.

Formation of a product with the structure of Formula I is enhanced by suitable dehydrating agents (e.g., acetic anhydride, trifluoroacetic anhydride, dicyclohexylcarbodiimide (DCC), triethylorthoformate and carbonyldiimidazole or a mixture of DCC and 1-hydroxybenzotriazole). This is accomplished by directly adding to the reaction mixture the dehydrating agent or, alternatively, by isolating the intermediates of Formula III and then treating those intermediates with the dehydrating agent in a separate reaction.

Compounds of Formula I in which X and/or Y substituents are present are conveniently prepared by introducing such substituents onto a diester of Formula II, i.e., a compound of Formula II in which $R^8$ and $R^9$ are alkoxy and Z is C=O, optionally converting the substituted diester to the corresponding dicarboxylic acid, and then reacting the substituted diester or dicarboxylic acid with an amine of the formula $R^1NH_2$ to form the corresponding substituted compound of Formula I.

Compounds of Formula I in which Z is C=O are prepared from compounds of Formula II in which Z is C=O. Compounds of Formula I in which Z is $CH_2$ are prepared from compounds of Formula II in which Z is $CH_2$. Compounds of Formula I in which Z is $CH_2$ are also prepared by reduction of the corresponding compound of Formula I in which Z is C=O. The reduction of a compound of Formula I in which Z is C=O to a compound of Formula I in which Z is $CH_2$ is described in Example 13.

In general, the starting materials utilized in Scheme I are themselves commercially available or the preparation thereof is known to those of ordinary skill in the art. For example optionally substituted 1,8-naphthalic anhydrides (i.e., compounds of Formula II in which $R^8$ and $R^9$ are together oxa and Z is C=O) may be prepared by oxidation of the correspondingly substituted or unsubstituted acenaphthene (Dashevskii, M. M.; Karishn, V. P. Org. Chim. Ind. 1937, 4, 406; Graebe, C. Annalen 1903, 327,77).

Compounds of Formula I are also prepared by the reaction sequence shown below in Scheme II.

SCHEME II

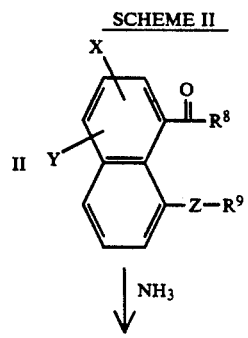

-continued
SCHEME II

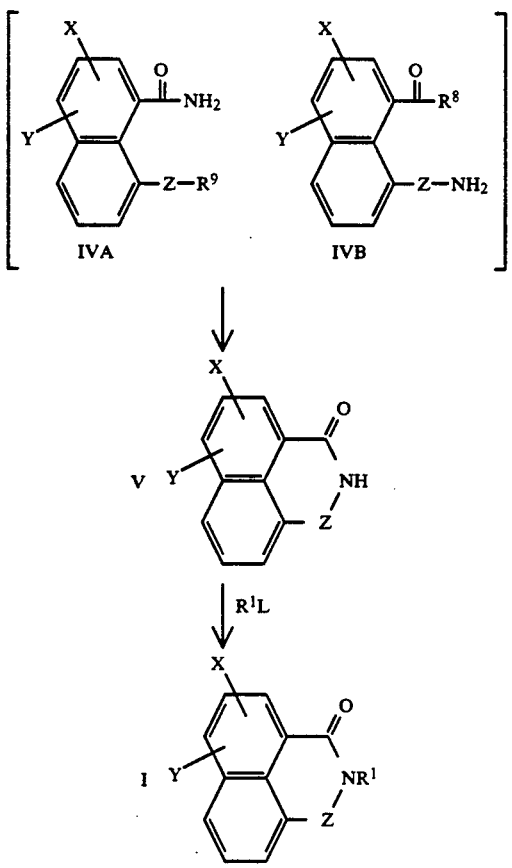

in which $R^8$ and $R^9$ are independently hydroxy, alkoxy, or halogen or are together oxa, L is a leaving group, and X, Y, Z, and $R^1$ are as defined in the Summary of the Invention, with the processes applying particularly well to the presently preferred embodiments.

Scheme II

Compounds of Formula I are also prepared by a two-step synthesis comprising (1) converting a compound of Formula II to an unsubstututed amide of Formula V and (2) condensing the unsubstituted amide of Formula V with an alkylating agent of the formula $R^1L$ to form a compound of Formula I.

Step 1

Compounds of Formula V are prepared by proceeding as in Step 1 of Scheme I but replacing the substituted amine with ammonia. Alternatively, intermediates of Formulae IVA and IVB are isolated and then converted to a compound of Formula V in a separated reaction.

Step 2

The alkylation reaction are carried out by reacting, in the presence of a strong base, a compound of Formula V with the appropriate alkylating agent. The reaction is carried out under standard amide alkylating conditions (Luh, T.; Fung S. H. Synth. Commun. 1979, 9, 757) in an inert solvent at a reaction temperature of 20° C. to 100° C. Appropriate bases include sodium or sodium hydride and are usually employed in molar excess. Suitable solvents include tetrahydrofuran or N,N-dialkylformamides such as N,N-dimethylformamide.

Alternatively, the alkylation is carried out with a phase-transfer catalyst (PTC) system, i.e., with catalyst in a liquid-liquid two phase solvent system (Gajda, T.; Zwierzak, A. Synthesis, Communications 1981, 1005), or preferably a solid-liquid system (Yamawaki, J.; Ando, T.; Hanafusa, T. Chem. Lett. 1981, 1143; Koziara, A.; Zawaszki, S.; Zwierzak, A. Synthesis 1979, 527, 549).

A liquid-liquid two-phase system is comprised of an aqueous phase consisting of a concentrated alkali hydroxide solution (e.g., 50% aqueous sodium hydroxide), an organic phase comprised of an inert water-immiscible organic solvent solvent, and an appropriate catalyst. A solid-liquid system consists of a powdered alkali hydroxide/alkali carbonate suspended in an organic solvent and catalyst.

The reaction is effected by slowing adding the alkylating agent to a PTC system containing a compound of Formula V until the alkylating agent is 10 to 50% in excess. The reaction mixture is kept at reflux until the reaction is complete. The mixture is then cooled to room temperature and the compound of Formula I is isolated by conventional methods. Suitable organic solvents include benzene, toluene, and the like. Appropriate catalysts include alumina coated with potassium fluoride and quaternary ammonium sulfates such as tetra-n-butyl-ammonium hydrogen sulfate and tricaprylylmethylammonium chloride.

A variation of Scheme II comprises isolating the intermediates of Formulae IVA and IVB, converting them to compounds of Formulae IIIA and IIIB by one of the above described alkylation processes and then dehydrating to form a compound of Formula I.

Additional Processes

Compounds of Formula I in which X and/or Y are $NH_2$ are prepared by the reduction of the corresponding compound of Formula I in which X is nitro. The reduction is carried out with an appropriate catalyst, preferably palladium on carbon, or by a selective chemical reduction, e.g., by reaction with stannous chloride or zinc/hydrochloric acid. The catalytic reduction of a compound of Formula I in which X is nitro to a compound in which X is amino is described in Example 7. The preparation of a compound of Formula I in which X is amino by chemical reduction is described in Example 8.

Compounds of Formula I in which X and/or Y are alkoxy or alkylamino are prepared by substitution of a corresponding nitro or halo substituent; or wherein X and/or Y is hydroxy, by the de-alkylation of a corresponding alkoxy substituent. The preparation of a compound of Formula I in which X is alkylamino is described in Example 5.

Furthermore, compounds of Formula I wherein Y is Cl, Br, I or $NO_2$ may be prepared by the introduction of such substituent onto a ring activated by a X substituent such as amino, (lower alkyl)amino, di(lower alkyl)amino, (lower alkanoyl)amino, hydroxy or alkoxy; or wherein X and/or Y is an acylamido substituent, by the acylation of a corresponding amino substituent. The preparation of a compound of Formula I in which X is amino and Y is chloro is described in Examples 9 and 10.

Compounds of Formula I in which $R^2$ or $R^5$ is not hydrogen are conveniently prepared by alkylation of compounds of Formula I in which $R^2$ or $R^5$ is hydrogen. The alkylation is carried out by reductive acylation, i.e., a reaction in the presence of a reducing agent, e.g., sodium cyanoborohydride, with a suitable aldehyde or ketone; or by reaction in the presence of a base, e.g., triethylamine, with an alkylating agent of the formula $R^2L$ or $R^5L$ in which $R^2$ and $R^5$ are any of the alkyl radicals defined for $R^2$ and $R^5$ in the Summary of the Invention and L is a leaving group. The preparation of a compound of Formula I by reductive acylation is described in Example 11. The preparation of a compound of Formula I in which the alkylating agent is allyl bromide is described in Example 12. All of the additional processes described above can be performed by methods well known to one of ordinary skill in the art of organic synthesis.

Compounds of Formula I wherein p is 1 (compounds of Formula I wherein the cyclic amine portion of $R^1$ is in the N-oxide form) may be prepared by oxidation of the corresponding compound of Formula I wherein p is 0, preferably nonsalt form. The oxidation is carried out at a reaction temperature of approximately 0° C. with an appropriate oxidizing agent and in a suitable inert, organic solvent. Suitable oxidizing agents include hydrogen peroxide or peroxy acids such as trifluoroperacetic acid, permaleic acid, perbenzoic acid, peracetic acid, and m-chloroperoxybenzoic acid. Suitable solvents include halogenated hydrocarbons, e.g., dichloromethane, and alcohols. Alternatively, the compounds of Formula I wherein p is 1 may be prepared using N-oxide derivatives of the starting materials or intermediates.

Compounds of Formula I wherein p is 0 (compounds of Formula I wherein the cyclic amine portion of $R^1$ is not in the N-oxide form) are also prepared by reduction of the corresponding compound of Formula I wherein p is 1. The reduction is carried out under standard conditions with an appropriate reducing agent in a suitable solvent. The mixture is occasionally agitated while the reaction temperature is gradually increased over a range of 0° C. to 80° C. Appropriate reducing agents include sulfur, sulfur dioxide, triarylphosphines (e.g., triphenylphosphine), alkali borohydrides (e.g., lithium borohydride, sodium borohydride, etc.), phosphorus trichloride and tribromide. Suitable solvents include acetonitrile, ethanol or aqueous dioxane.

As will be apparent to one of ordinary skill in the art, compounds of Formula I may be prepared as individual isomers or mixtures of isomers. Isomers which are diastereomers have distinct physical properties (e.g., melting points, boiling points, solubilities, reactivity, etc.) and are readily separated by taking advantage of these dissimilarities. For example, diastereomers can be separated by chromatography or, preferably, by separation/resolution techniques based upon differences in solubility. Optical isomers can be separated by reacting the racemic mixture with an optically active resolving agent to form a pair of diastereomeric compounds. The isomers are then separated by any of the techniques described above for the separation of diastereomers and the pure optical isomer recovered, along with the resolving agent, by any practical means that would not result in racemization. While resolution of optical isomers can be carried out using covalent diastereomeric derivatives of compounds of Formula I, dissociable complexes are preferred, e.g., crystalline diastereomeric salts. Suitable resolving acids include tartaric acid, o-nitrotartranilic acid, mandelic acid, malic acid, the 2-arylpropionic acids in general, and camphorsulfonic acid.

Individual isomers of compounds of Formula I can also be separated by such methods as direct or selective crystallization or by any other method known to one of ordinary skill in the art. A more detailed description of the techniques applicable to the resolution of stereoisomers of compounds of Formula I can be found in Jean Jacques; Andre Collet; Samuel H. Wilen Enantiomers, Racemates and Resolutions 1981, John Wiley & Sons, Inc. Alternatively, individual isomers of compounds of Formula I can be prepared using the isomeric forms of the starting materials.

Compounds of Formula I are converted to a corresponding acid addition salt with a pharmaceutically acceptable inorganic or organic acid. In addition, pharmaceutically acceptable salts may be formed when acidic protons present are capable of reacting with inorganic or organic bases. Inorganic and organic acids and bases suitable for the preparation of the pharmaceutically acceptable salts of compounds of Formula I are set forth in the definitions section of this application.

Compounds of Formula I in the acid addition salt form are converted to the corresponding free base by treatment with a suitable base such as ammonium hydroxide solution, sodium hydroxide or the like. Compounds of Formula I in which acidic protons form salts are converted to the corresponding Compounds of Formula I by treatment with a suitable acid such as hydrochloric acid.

Of the two processes for synthesizing compounds of Formula I described within this application, Scheme I is preferred. While compounds of Formula I may be synthesized by the process described in Scheme II, the alkylation step therein may require severe reaction conditions and is usually restricted to alkylation of unsubstituted amides with primary alkylating agents, e.g., $CH_3L$.

In summary, the processes for preparing the compounds of Formula I are:

(1) reacting a compound of Formula II with a substituted amine of the formula $R^1NH_2$ to form a compound of Formula I or reacting a compound of Formula V with an alkylating agent of the formula $R^1L$ to form a compound of Formula I;

(2) optionally isolating intermediates of Formulae IIIA and IIIB formed by reacting a compound of Formula II with a substituted amine of the formula $R^1NH_2$ and subsequently converted the intermediates to a compound of Formula I.

(3) optionally reducing a compound of Formula I in which Z is C=O to the corresponding compound of Formula I in which Z is $CH_2$;

(4) optionally reducing a compound of Formula I in which X and/or Y is nitro to the corresponding compound of Formula I in which X and/or Y is amino;

(5) optionally reacting an alkylating agent of the formula $R^2L$ or $R^5L$ in which $R^2$ and $R^5$ are as defined above, except $R^2$ or $R^5$ is not hydrogen, and L is a leaving group with a compound of Formula I in which $R^2$ or $R^5$ is hydrogen to form a compound of Formula I in which $R^2$ or $R^5$ is not hydrogen;

(6) optionally reductively reacting an aldehyde or ketone, with a compound of Formula I in which $R^2$ or $R^5$ is hydrogen to form a compound of Formula I in which $R^2$ or $R^5$ is not hydrogen;

(7) optionally introducing a Y substituent onto a compound of Formula I activated by a X substituent to form a compound of Formula I in which Y is NH₂, Cl, Br, I or NO₂;

(8) optionally acylating a compound of Formula I in which X and/or Y are nitro to form compounds of Formula I in which X and/or Y are acetamido;

(9) optionally converting a compound of Formula I in which X and/or Y are nitro or halogen to the corresponding compound of Formula I in which X and/or Y substituents are alkoxy or alkylamino;

(10) optionally converting a compound of Formula I to a corresponding pharmaceutically acceptable salt;

(11) optionally converting a salt of a compound of Formula I to the corresponding compound of Formula I;

(12) optionally oxidizing a compound of Formula I in which p is 0 to the corresponding N-oxide;

(13) optionally reducing the N-oxide of a compound to the corresponding compound of Formula I in which p is 0; or

(14) optionally separating a mixture of isomers of a compound of Formula I into a single isomer.

In any of the above last step processes, a reference to Formula I, II, III or IV refers to such Formula wherein X, Y, Z, R¹, R², R³, R⁴, R⁵, R⁶, R⁷, p and n are as defined in their broadest definitions set forth in the Summary of the Invention, with the processes applying particularly well to the presently preferred embodiments.

EXAMPLE 1

(RS)-2-(1-azabicyclo[2.2.2]oct-3-yl)-2,3-dihydro-1H-benz[de]isoquinoline-1,3-dione The following is the preparation of a compound of Formula I via Scheme I in which p is 0;
Z is C=O;
X and Y are hydrogen; and
R¹ is 1-azabicyclo[2.2.2]oct-3-yl.

A solution of 1,8-naphthalic anhydride (1.9 g, 9.6 mmol) and (RS)-3-amino-1-azabicyclo[2.2.2]octane (1.2 g, 9.5 mmol) in n-butanol (100 mL) was stirred for 3 hours at reflux temperature and the solution concentrated to dryness. Purification of the remaining solid by column chromatography (silica-gel; 5-10% gradient methanol in CH₂Cl₂ and approximately 1% aqueous NH₄OH) gave (RS)-2-(1-azabicyclo[2.2.2]oct-3-yl)-2,3-dihydro-1H-benz[de]isoquinoline-1,3-dione (2.45 g, 7.95 mmol), m.p. 206°-207° C.

Formation of the hydrochloride salt from ethanol containing hydrogen chloride gave (RS)-2-(1-azabicyclo[2.2.2]oct-3-yl)-2,3-dihydro-1H-benz[de]isoquinoline-1,3-dione hydrochloride, m.p. 340°-342° C.

Proceeding as in Example 1, but replacing (RS)-3-amino-1-azabicyclo[2.2.2]octane with (S)-3-amino-1-azabicyclo[2.2.2]octane, gave (S)-2-(1-azabicyclo[2.2.2]oct-3-yl)-2,3-dihydro-1H-benz[de]isoquinoline-1,3-dione, m.p. 185°-189° C., $[\alpha]_D^{25} - 73.8°$ (c=0.4, CHCl₃) and (S)-2-(1-azabicyclo[2.2.2]oct-3-yl)-2,3-dihydro-1H-benz[de]isoquinoline-1,3-dione hydrochloride, m.p. 323°-324° C., $[\alpha]_D^{25} - 30.6°$ (c=0.565, MeOH).

Proceeding as in Example 1, but replacing 1,8-naphthalic anhydride with 4-bromo-1,8-naphthalic anhydride, gave (RS)-2-(1-azabicyclo[2.2.2]oct-3-yl)-6-bromo-2,3-dihydro-1H-benz[de]isoquinoline-1,3-dione, m.p. 305°-308° C.

Proceeding as in Example 1, but replacing 1,8-naphthalic anhydride with 4-chloro-1,8-naphthalic anhydride, gave (RS)-2-(1-azabicyclo[2.2.2]oct-3-yl)-6-chloro-2,3-dihydro-1H-benz[de]isoquinoline-1,3-dione, m.p. 226°-229° C. and (RS)-6-chloro-2-(1-azabicyclo[2.2.2]oct-3-yl)-2,3-dihydro-1H-benz[de]isoquinoline-1,3-dione hydrochloride, m.p. 350°-352° C.

Proceeding as in Example 1 the following are prepared: (R)-2-(1-azabicyclo[2.2.2]oct-3-yl)-2,3-dihydro-1H-benz[de]isoquinoline-1,3-dione; 2-(1-azabicyclo[2.2.2]oct-4-yl)-2,3-dihydro-1H-benz[de]isoquinoline-1,3-dione; 2,3-dihydro-2-(1-methylpiperidin-4-yl)-1H-benz[de]isoquinoline-1,3-dione; (S)-2,3-dihydro-2-(1-methylpiperidin-3-yl)-1H-benz[de]isoquinoline-1,3-dione; (R)-2,3-dihydro-2-(1-methylpiperidin-3-yl)-1H-benz[de]isoquinoline-1,3-dione; (RS)-2,3-dihydro-2-(1-methylpiperidin-3-yl)-1H-benz[de]isoquinoline-1,3-dione; 2,3-dihydro-2-(endo-9-methyl-9-azabicyclo[3.3.1]non-3-yl)-1H-benz[de]isoquinoline-1,3-dione; 2,3-dihydro-2-(exo-9-methyl-9-azabicyclo[3.3.1]non-3-yl)-1H-benz[de]isoquinoline-1,3-dione; 2,3-dihydro-2-(endo-8-methyl-8-azabicyclo[3.2.1]oct-3-yl)-1H-benz[de]isoquinoline-1,3-dione; 2,3-dihydro-2-(exo-8-methyl-8-azabicyclo[3.2.1]oct-3-yl)-1H-benz[de]isoquinoline-1,3-dione; (S)-2-(endo-1-azabicyclo[3.3.1]non-4-yl)-2,3-dihydro-1H-benz[de]isoquinoline-1,3-dione; (R)-2-(endo-1-azabicyclo[3.3.1]non-4-yl)-2,3-dihydro-1H-benz[de]isoquinoline-1,3-dione; (RS)-2-(endo-1-azabicyclo[3.3.1]non-4-yl)-2,3-dihydro-1H-benz[de]isoquinoline-1,3-dione; (S)-2-(exo-1-azabicyclo[3.3.1]non-4-yl)-2,3-dihydro-1H-benz[de]isoquinoline-1,3-dione; (R)-2-(exo-1-azabicyclo[3.3.1]non-4-yl)-2,3-dihydro-1H-benz[de]isoquinoline-1,3-dione; and (RS)-2-(exo-1-azabicyclo[3.3.1]non-4-yl)-2,3-dihydro-1H-benz[de]isoquinoline-1,3-dione.

EXAMPLE 2

(S)-2-(1-azabicyclo[2.2.2]oct-3-yl)-2,3-dihydro-6-nitro-1H-benz[de]isoquinoline-1,3-dione The following is the preparation of a compound of Formula I via Scheme I in which p is 0;
Z is C=O;
X is nitro at the 6-position;
Y is hydrogen; and
R¹ is 1-azabicyclo[2.2.2]oct-3-yl.

A solution of (S)-3-amino-1-azabicyclo[2.2.2]octane (3.1 g; 24.6 mmol) in xylenes (40 mL) was added dropwise to a boiling solution of 4-nitro-1,8-naphthalic anhydride (6.1 g; 25.1 mmol). The reaction mixture was kept at reflux temperature for 6 hours while the water that formed was collected in a Dean-Stark trap. Acetic anhydride (1.5 mL; 13.0 mmol) was added and the mixture heated for an additional 16 hours. The solvent was evaporated in vaccuo. Purification by column chromatography (silica-gel; 5% methanol in CH₂Cl₂ and approximately 1% aqueous NH₄OH) gave (S)-2-(1-azabicyclo[2.2.2]oct-3-yl)-2,3-dihydro-6-nitro-1H-benz[de]isoquinoline-1,3-dione (6.0 g; 16.8 mmol), m.p. 214°-219° C.

Proceeding as in Example 2, but replacing (S)-3-amino-1-azabicyclo[2.2.2]octane with (RS)-3-amino-1-azabicyclo[2.2.2]octane, gave (RS)-2-(1-azabicyclo[2.2.2]oct-3-yl)-2,3-dihydro-6-nitro-1H-benz[de]isoquinoline-1,3-dione, m.p. 224°-226° C. and (RS)-2-(1-azabicyclo[2.2.2]oct-3-yl)-2,3-dihydro-6-nitro-1H-benz[de]isoquinoline-1,3-dione hydrochloride, m.p. >330° C.

Proceeding as in Example 2, but replacing (S)-3-amino-1-azabicyclo[2.2.2]octane with (R)-3-amino-1- azabicyclo[2.2.2]octane, gave (R)-2-(1-azabicyclo[2.2.2-]oct-3-yl)-2,3-dihydro-6-nitro-1H-benz[de]isoquinoline-1,3-dione, m.p. 216°–220° C.

Proceeding as in Example 2, but replacing (S)-3-amino-1-azabicyclo[2.2.2]octane with (endo)-3-amino-8-methyl-8-azabicyclo[3.2.1]octane, gave 2-(endo-8-methyl-8-azabicyclo[3.2.1]oct-3-yl)-2,3-dihydro-6-nitro-1H-benz[de]isoquinoline-1,3-dione.

Proceeding as in Example 2 the following are prepared: 2-(1-azabicyclo[2.2.2]oct-4-yl)-2,3-dihydro-6-nitro-1H-benz[de]isoquinoline-1,3-dione; 2,3-dihydro-2-(endo-9-methyl-9-azabicyclo[3.3.1]non-3-yl)-6-nitro-1H-benz[de]isoquinoline-1,3-dione; 2,3-dihydro-2-(exo-9-methyl-9-azabicyclo[3.3.1]non-3-yl)-6-nitro-1H-benz[de]isoquinoline-1,3-dione; 2,3-dihydro-2-(exo-8-methyl-8-azabicyclo[3.2.1]oct-3-yl)-6-nitro-1H-benz[de]isoquinoline-1,3-dione; (S)-2-(endo-1-azabicyclo[3.3.1]non-4-yl)-2,3-dihydro-6-nitro-1H-benz[de]isoquinoline-1,3-dione; (R)-2-(endo-1-azabicyclo[3.3.1]non-4-yl)-2,3-dihydro-6-nitro-1H-benz[de]isoquinoline-1,3-dione; (RS)-2-(endo-1-azabicyclo[3.3.1]non-4-yl)-2,3-dihydro-6-nitro-1H-benz[de]isoquinoline-1,3-dione; (S)-2-(exo-1-azabicyclo[3.3.1]non-4-yl)-2,3-dihydro-6-nitro-1H-benz[de]isoquinoline-1,3-dione; (R)-2-(exo-1-azabicyclo[3.3.1]non-4-yl)-2,3-dihydro-6-nitro-1H-benz[de]isoquinoline-1,3-dione; and (RS)-2-(exo-1-azabicyclo[3.3.1]non-4-yl)-2,3-dihydro-6-nitro-1H-benz[de]isoquinoline-1,3-dione.

EXAMPLE 3

2,3-dihydro-2-(1-methylpiperidin-4-yl)-6-nitro-1H-benz[de]isoquinoline-1,3-dione The following is the preparation of a compound of Formula I via Scheme I in which p is 0;
Z is C=O;
X is nitro at the 6-position;
Y is hydrogen; and
$R^1$ is 1-methylpiperidin-4-yl.

4-Amino-1-methylpiperidine (12.3 g; 107.8 mmol) and 4-nitro-1,8-naphthalic anhydride (26.2 g; 107.8 mmol) in ethanol (700 mL) was kept at reflux temperature for 24 hours. The reaction mixture was then cooled and concentrated to dryness. The residue was stirred with methylene chloride (500 mL) and the mixture filtered. Purification of the filtrate by column chromatography (silica-gel; 5% methanol in $CH_2Cl_2$ and approximately 1% aqueous $NH_4OH$) gave 2,3-dihydro-2-(1-methylpiperindin-4-yl)-6-nitro-1H-benz[de]isoquinoline-1,3-dione (15.2 g; 44.8 mmol), m.p. 215°–217° C. Anal.: Calcd. for $C_{16}H_{16}N_3O_4$: C, 63.71; H, 5.05; N, 12.38. Found: C, 63.65; H, 5.01; N, 12.29.

Formation of the hydrochloride salt from ethanol containing hydrogen chloride gave 2,3-dihydro-2-(1-methylpiperindin-4-yl)-6-nitro-1H-benz[de]isoquinoline-1,3-dione hydrochloride (11.5 g; 33.9 mmol).

Proceeding as in Example 3, but replacing 4-nitro-1,8-naphthalic anhydride with 1,8-naphthalic anhydride gave 2,3-dihydro-2-(1-methylpiperidin-4-yl)-1H-benz[de]isoquinoline-1,3-dione, m.p. 320°–323° C.

Proceeding as in Example 3, but replacing 4-amino-1-methylpiperidine with 4-amino-1-benzylpiperidine gave 2-(1-benzylpiperidin-4-yl)-2,3-dihydro-6-nitro-1H-benz[de]isoquinoline-1,3-dione hydrochloride, m.p. 254°–255° C.

Proceeding as in Example 3, but replacing 4-amino-1-methylpiperidine with 4-amino-1-(3-(4-fluorophenoxy)propyl)piperidine gave 2-(1-(3-(4-fluorophenoxy)propyl)piperidin-4-yl)-2,3-dihydro-6-nitro-1H-benz[de]isoquinoline-1,3-dione hydrochloride, m.p. 247° C.

Proceeding as in Example 3, but replacing 4-amino-1-methylpiperidine with 4-amino-2,2,6,6-tetramethylpiperidine gave 2,3-dihydro-2-(2,2,6,6-tetramethylpiperidin-4-yl)-6-nitro-1H-benz[de]isoquinoline-1,3-dione hydrochloride, m.p. >320° C.

Proceeding as in Example 3, the following are prepared: (S)-2,3-dihydro-2-(methylpiperidin-3-yl)-6-nitro-1H-benz[de]isoquinoline-1,3-dione; (R)-2,3-dihydro-2-(methylpiperidin-3-yl)-6-nitro-1H-benz[de]isoquinoline-1,3-dione; and (RS)-2,3-dihydro-2-(methylpiperidin-3-yl)-6-nitro-1H-benz[de]isoquinoline-1,3-dione.

EXAMPLE 4

(S)-2-(1-azabicyclo[2.2.2]oct-3-yl)-2,3-dihydro-6-nitro-1H-benz[de]isoquinoline-1,3-dione The following is the preparation of a compound of Formula I via Scheme I in which p is 0;
Z is C=O;
X is nitro at the 8-position;
Y is hydrogen; and
$R^1$ is 1-azabicyclo[2.2.2]oct-3-yl.

A solution of (S)-3-amino-1-azabicyclo[2.2.2]octane (7.5 g; 59.5 mmol) in toluene (100 mL) was added in a thin stream to a suspension of 4-nitro-1,8-naphthalic anhydride (14.5 g; 59.6 mmol) in toluene (250 mL) at reflux temperature. The reaction mixture was maintained at reflux temperature for 15 minutes and then allowed to cool to ambient temperature. Evaporation of the solvent gave intermediate(s) (S)-8-(1-azabicyclo[2.2.2.]oct-3-yl)-aminocarbonyl-4-nitronaphthalene-1-carboxylic acid and/or (S)-8-(1-azabicyclo[2.2.2.]oct-3-yl)aminocarbonyl-5-nitronaphthalene-1-carboxylic acid (18.8 g; 57.7 mmol), m.p. 172°–175° C.

A mixture of the intermediate(s) (17.05 g; 52.3 mmol) and carbonyldiimidazole (8.7 g; 53.7 mmol) in $CH_2Cl_2$ (500 mL) was stirred at room temperature for 16 hours. The reaction mixture was washed with water containing 5% $NaHCO_3$ (2×200 mL), dried over $K_2CO_3$, and then filtered. Evaporation of the solvents gave (S)-2-(1-azabicyclo[2.2.2.]oct-3-yl)-2,3-dihydro-6-nitro-1H-benz[de]isoquinoline-1,3-dione (5.3 g, 17.2 mmol), m.p. 214°–219° C.

EXAMPLE 5

2,3-dihydro-6-methylamino-2-(1-methylpiperidin-4-yl)-1H-benz[de]isoquinoline-1,3-dione The following is the preparation of a compound of Formula I via Scheme I in which p is 0;
Z is C=O;
X is methylamino at the 6-position;
Y is hydrogen; and
$R^1$ is 1-methylpiperidin-4-yl.

A mixture of 40% aqueous methylamine (2 mL) and 2,3-dihydro-2-(1-methylpiperidin-4-yl)-6-nitro-1H-benz[de]isoquinoline-1,3-dione (1.1 g; 3.14 mmol), prepared as in Example 3, in isopropanol (10 mL) was stirred at 65°–70° C. for six hours. Concentration of the solution followed by purification of the residue by column chromatography (silica-gel; 3% methanol in $CH_2Cl_2$ and approximately 1% aqueous $NH_4OH$) gave 2,3-dihydro-6-methyamino-2-(1-methylpiperidin-4-yl)-

1H-benz[de]isoquinoline-1,3-dione (0.63 g; 1.95 mmol) as a yellow precipitate, m.p. 251°–254° C.

Formation of the hydrochloride salt from ethanol containing hydrogen chloride gave 2,3-dihydro-6-methylamino-2-(1-methylpiperidin-4-yl)-1H-benz[de]isoquinoline-1,3-dione hydrochloride (0.68 g; 1.89 mmol), m.p.>320° C. Anal.: Calcd. for $C_{19}H_{22}N_3O_2Cl0.33\ H_2O$: C, 62.38; H, 6.24; N, 11.49. Found: C, 62.42; H, 6.42; N, 11.21.

Proceeding as in Example 5, but replacing methylamine with dimethylamine gave 2,3-dihydro-6-dimethyamino-2-(1-methylpiperidin-4-yl)-1H-benz[de]isoquinoline-1,3-dione, m.p.>150° C.

Proceeding as in Example 5 the following are prepared: (S)-2-(1-azabicyclo[2.2.2]oct-3-yl)-2,3-dihydro-6-methylamino-1H-benz[de]isoquinoline-1,3-dione; (R)-2-(1-azabicyclo[2.2.2]oct-3-yl)-2,3-dihydro-6-methylamino-1H-benz[de]isoquinoline-1,3-dione; (RS)-2-(1-azabicyclo[2.2.2]oct-3-yl)-2,3-dihydro-6-methylamino-1H-benz[de]isoquinoline-1,3-dione; 2-(1-azabicyclo[2.2.2]oct-4-yl)-2,3-dihydro-6-methylamino-1-H-benz[de]isoquinoline-1,3-dione; (S)-2,3-dihydro-6-methylamino-2-(1-methylpiperidin-3-yl)-1H-benz[de]isoquinoline-1,3-dione; (R)-2,3-dihydro-6-methylamino-2-(1-methylpiperidin-3-yl)-1H-benz[de]isoquinoline-1,3-dione; (RS)-2,3-dihydro-6-methylamino-2-(1-methylpiperidin-3-yl)-1H-benz[de]isoquinoline-1,3-dione; 2,3-dihydro-6-methylamino-2-(endo-9-methyl-9-azabicyclo[3.3.1]non-3-yl)-1H-benz[de]isoquinoline-1,3-dione; 2,3-dihydro-6-methylamino-2-(exo-9-methyl-9-aza-bicyclo[3.3.1]non-3-yl)-1H-benz[de]isoquinoline-1,3-dione; 2,3-dihydro-6-methylamino-2-(endo-8-methyl-8-azabicyclo[3.2.1]oct-3-yl)-1H-benz[de]isoquinoline-1,3-dione; 2,3-dihydro-6-methylamino-2-(exo-8-methyl-8-azabicyclo[3.2.1]oct-3-yl)-1H-benz[de]isoquinoline-1,3-dione; (S)-2-(endo-1-azabicyclo[3.3.1]non-4-yl)-2,3-dihydro-6-methylamino-1H-benz[de]isoquinoline-1,3-dione; (R)-2-(endo-1-azabicyclo[3.3.1]non-4-yl)-2,3-dihydro-6-methylamino-1H-benz[de]isoquinoline-1,3-dione; (RS)-2-(endo-1-azabicyclo[3.3.1]non-4-yl)-2,3-dihydro-6-methylamino-1H-benz[de]isoquinoline-1,3-dione; (S)-2-(exo-1-azabicyclo[3.3.1]non-4-yl)-2,3-dihydro-6-methylamino-1H-benz[de]isoquinoline-1,3-dione; (R)-2-(exo-1-azabicyclo[3.3.1]non-4-yl)-2,3-dihydro-6-methylamino-1H-benz[de]isoquinoline-1,3-dione; and (RS)-2-(exo-1-azabicyclo[3.3.1]non-4-yl)-2,3-dihydro-6-methylamino-1H-benz[de]isoquinoline-1,3-dione.

EXAMPLE 6

(S)-6-amino-2-(1-azabicyclo[2.2.2]oct-3-yl)-2,3-dihydro-1H-benz[de]isoquinoline-1,3-dione The following is the preparation of a compound of Formula I via Scheme I in which p is 0;
Z is C=O;
X is amino at the 6-position;
Y is hydrogen; and
$R^1$ is 1-azabicyclo[2.2.2]oct-3-yl.

A solution of (S)-2-(1-azabicyclo[2.2.2]oct-3-yl)-2,3-dihydro-6-nitro-1H-benz[de]isoquinoline-1,3-dione (3.2 g; 8.8 mmol), prepared as in Example 2, in acetic acid (80 mL) was hydrogenated at atmospheric pressure over 10% Pd/C catalyst (1.2 g) for 3 hours. The catalyst was removed by filtration, the filtrate concentrated to a small volume, and the residue dissolved in water. This aqueous solution was added dropwise to dilute $NH_4OH$ and the solid that precipitated was collected on a Buechner funnel. Drying under vacuum gave (S)-6-amino-2-(1-azabicyclo[2.2.2]oct-3-yl)-2,3-dihydro-1H-benz[de]isoquinoline-1,3-dione (2.57 g; 7.93 mmol), m.p. 305°–308° C., $[\alpha]_D^{25}$ −44.2° (c=0.373, MeOH).

Proceeding as in Example 6, but replacing (S)-2-(1-azabicyclo[2.2.2]oct-3-yl)-2,3-dihydro-6-nitro-1H-benz[de]isoquinoline-1,3-dione with (RS)-2-(1-azabicyclo[2.2.2]oct-3-yl)-2,3-dihydro-6-nitro-1H-benz[de]isoquinoline-1,3-dione, gave (RS)-6-amino-2-(1-azabicyclo[2.2.2]oct-3-yl)-2,3-dihydro-1H-benz[de]isoquinoline-1,3-dione dihydrochloride, m.p. 308°–312° C.

Proceeding as in Example 6, but replacing (S)-2-(1-azabicyclo[2.2.2]oct-3-yl)-2,3-dihydro-6-nitro-1H-benz[de]isoquinoline-1,3-dione with 2,3-dihydro-2-(endo-8-methyl-8-azabicyclo[3.2.1]oct-3-yl)-6-nitro-1H-benz[de]isoquinoline-1,3-dione, gave 6-amino-2,3-dihydro-2-(endo-8-methyl-8-azabicyclo[3.2.1]oct-3-yl)-1H-benz[de]isoquinoline-1,3-dione dihydrochloride, m.p. 327°–330° C.

Proceeding as in Example 6, but replacing (S)-2-(1-azabicyclo[2.2.2]oct-3-yl)-2,3-dihydro-6-nitro-1H-benz[de]isoquinoline-1,3-dione with (RS)-2-(1-azabicyclo[2.2.2]oct-3-yl)-2,3-dihydro-5-nitro-1H-benz[de]isoquinoline-1,3-dione, gave (RS)-5-amino-2-(1-azabicyclo[2.2.2]oct-3-yl)-2,3-dihydro-1H-benz[de]isoquinoline-1,3-dione dihydrochloride, m.p. 287°–293° C. Anal.: Calcd. for $C_{19}H_{21}Cl_2N_3O_2$: C, 57.88; H, 5.73; N, 10.65%. Found: C, 58.03; H, 5.54; N, 10.58%.

Proceeding as in Example 6 the following are prepared: (R)-6-amino-2-(1-azabicyclo[2.2.2]oct-3yl)-2,3-dihydro-1H-benz[de]isoquinoline-1,3-dione; 6-amino-2-(1-azabicyclo[2.2.2]oct-4-yl)-2,3-dihydro-1H-benz[de]isoquinoline-1,3-dione; 6-amino-2,3-dihydro-2-(endo-9-methyl-9-azabicyclo[3.3.1]non-3-yl)-1H-benz[de]isoquinoline-1,3-dione; 6-amino-2,3-dihydro-2-(exo-9-methyl-9-azabicyclo[3.3.1]non-3-yl)-1H-benz[de]isoquinoline-1,3-dione; 6-amino-2,3-dihydro-2-exo-8-methyl-8-azabicyclo[3.2.1]oct-3-yl)-1H-benz[de]isoquinoline-1,3-dione; (S)-6-amino-2-(endo-1-azabicyclo[3.3.1]non-4-yl)-2,3-dihydro-1H-benz[de]isoquinoline-1,3-dione; (R)-6-amino-2-(endo-1-azabicyclo[3.3.1]non-4-yl)-2,3-dihydro-1H-benz[de]isoquinoline-1,3-dione; (RS)-6-amino-2-(endo-1-azabicyclo[3.3.1]non-4-yl)-2,3-dihydro-1H-benz[de]isoquinoline-1,3-dione; (S)-6-amino-2-(exo-1-azabicyclo[3.3.1]oct-4-yl)-2,3-dihydro-1H-benz[de]isoquinoline-1,3-dione; (R)-6-amino-2-(exo-1-azabicyclo[3.3.1]non-4-yl)-2,3-dihydro-1H-benz[de]isoquinoline-1,3-dione; and (RS)-6-amino-2-(exo-1-azabicyclo[3.3.1]non-4-yl)-2,3-dihydro-1H-benz[de]isoquinoline-1,3-dione.

EXAMPLE 7

6-amino-2,3-dihydro-2-(1-methylpiperidin-4-yl)-1H-benz[de]isoquinoline-1,3-dione The following is the preparation of a compound of Formula I via Scheme I in which p is 0;
Z is C=O;
X is amino at the 6-position;
Y is hydrogen; and
$R^1$ is 1-methylpiperidin-4-yl.

A mixture of 2,3-dihydro-2-(1-methyl-piperidin-4-yl)-6-nitro-1H-benz[de]isoquinoline-1,3-dione (11.5 g; 33.9 mmol), prepared as in Example 3, in water (150 mL) and methanol (350 mL) was hydrogenated at atmospheric pressure over 10% Pd/C catalyst (1.4 g) for 5 hours. The catalyst was removed by filtration and the filtrate concentrated to a small volume. Isopropanol was added and the solution concentrated. Isopropanol was again added to the residue and the solution reconcentrated. The residue was swirled in ethanol and ether and the solid residue collected on a Buechner funnel. Drying under vacuum gave 6-amino-2,3-dihydro-2-(1-methylpiperidin-4-yl)-1H-benz[de]isoquinoline-1,3-dione (9.34 g; 27.0 mmol), m.p 345°-348° C.

Proceeding as in Example 7, but replacing 2,3-dihydro-2-(1-methylpiperidin-4-yl)-6-nitro-1H-benz[de]isoquinoline-1,3-dione with 2-(1-benzylpiperidin-4-yl)-2,3-dihydro-6-nitro-1H-benz[de]isoquinoline-1,3-dione, gave 6-amino-2-(1-benzylpiperidin-4-yl)-2,3-dihydro-1H-benz[de]isoquinoline-1,3-dione.

Proceeding as in Example 7, but replacing 2,3-dihydro-2-(1-methylpiperidin-4-yl)-6-nitro-1H-benz[de]isoquinoline-1,3-dione with 2-(1-(3-(4-fluorophenoxy)propyl)piperidin-4-yl)-2,3-dihydro-6-nitro-1H-benz[de]isoquinoline-1,3-dione, gave 6-amino-2-(1-(3-(4-fluorophenoxy)propyl)piperidin-4-yl)-2,3-dihydro-1H-benz[de]isoquinoline-1,3-dione hydrochloride, m.p. >170° C.

Proceeding as in Example 7, but replacing 2,3-dihydro-2-(1-methylpiperidin-4-yl)-6-nitro-1H-benz[de]isoquinoline-1,3-dione with 2,3-dihydro-2-(2,2,6,6-tetramethylpiperidin-4-yl)-6-nitro-1H-benz[de]isoquinoline-1,3-dione, gave 6-amino-2,3-dihydro-2-(2,2,6,6-tetramethylpiperidin-4-yl)-1H-benz[de]isoquinoline-1,3-dione hydrochloride, m.p. >280° C.

Proceeding as in Example 7, the following are prepared: (S)-6-amino-2,3-dihydro-2-(methylpiperidin-3-yl)-1H-benz[de]isoquinoline-1,3-dione (R)-6-amino-2,3-dihydro-2-(methylpiperidin-3-yl)-1H-benz[de]isoquinoline-1,3-dione; and (RS)-6-amino-2,3-dihydro-2-(methylpiperidin-3-yl)-1H-benz[de]isoquinoline-1,3-dione.

EXAMPLE 8

6-amino-2-(1-benzylpiperidin-4-yl)-2,3-dihydro-1H-benz[de]isoquinoline-1,3-dione The following is the preparation of a compound of Formula I via Scheme I in which
p is 0;
Z is C=O;
X is amino at the 6-position;
Y is chloro; and
R¹ is 1-benzylpiperidin-4-yl.

To a solution of stannous chloride (5.0 g; 22.2 mmol) and 2-(1-benzylpiperidin-4-yl)-2,3-dihydro-6-nitro-1H-benz[de]isoquinoline-1,3-dione (1.9 g; 4.75 mmol), prepared as in Example 3, in glacial acetic acid (5 mL) was added 10% hydrochloric acid (7 mL). The reaction mixture was stirred for 2 hours and then a mixture of 10% sodium hydroxide and methylene chloride was added. The aqueous layer was extracted three additional times with methylene chloride and then the combined extracts were dried over potassium carbonate. Filtration and concentration of the methylene chloride extracts gave 6-amino-2-(1-benzylpiperidin-4-yl)-2,3-dihydro-1H-benz[de]isoquinoline-1,3-dione (1.5 g; 3.90 mmol), m.p. 226°-228° C. Anal.: Calcd. for $C_{21}H_{21}N_3O_3Cl_2 \cdot 0.333 H_2O$: C, 57.30; H, 4.96; N, 9.54. Found: C, 57.39; H, 5.06; N, 9.52.

EXAMPLE 9

(RS)-6-amino-2-(1-azabicyclo[2.2.2.]oct-3-yl)-5-chloro-2,3-dihydro-1H-benz[de]isoquinoline-1,3-dione The following is the preparation of a compound of Formula I via Scheme I in which
p is 0;
Z is C=O;
X is amino at the 6-position;
Y is chloro at the 5-position; and
R¹ is 1-azabicyclo[2.2.2]oct-3-yl.

A solution of (RS)-6-amino-2-(1-azabicyclo[2.2.2.]oct-3-yl)-2,3-dihydro-1H-benz[de]isoquinoline-1,3-dione (0.5 g; 1.55 mmol), prepared as in Example 6, in acetic acid (10 mL) and acetonitrile (10 mL) was cooled in an ice-water bath and chlorine (1.7-1.8 mmol) in acetic acid was added. The reaction mixture was concentrated to a small volume and ammonium hydroxide was added to form a precipitate. Purification by column chromatography (silica gel; 10% methanol in CH₂Cl₂ and approximately 1% aqueous NH₄OH) gave (RS)-6-amino-2-(1-azabicyclo[2.2.2.]oct-3-yl)-5-chloro-2,3-dihydro-1H-benz[de]isoquinoline-1,3-dione (0.24 g; 0.67 mmol), m.p. >300° C.

Proceeding as in Example 9, but replacing (RS)-6-amino-2-(1-azabicyclo[2.2.2.]oct-3-yl)-2,3-dihydro-1H-benz[de]isoquinoline-1,3-dione with (S)-6-amino-2-(1-azabicyclo[2.2.2.]oct-3-yl)-2,3-dihydro-1H-benz[de]isoquinoline-1,3-dione, gave (S)-6-amino-2-(1-azabicyclo[2.2.2.]oct-3-yl)-5-chloro-2,3-dihydro-1H-benz[de]isoquinoline-1,3-dione, m.p. 215°-219° C., $[\alpha]_D^{25}$ −77° (c=0.645, EtOH) and (S)-6-amino-2-(1-azabicyclo[2.2.2.]oct-3-yl)-5-chloro-2,3-dihydro-1H-benz[de]isoquinoline-1,3-dione hydrochloride, m.p. 345°-349° C., $[\alpha]_D^{25}$ −34° (c=0.47, MeOH).

Proceeding as in Example 9, but replacing (RS)-6-amino-2-(1-azabicyclo[2.2.2.]oct-3-yl)-2,3-dihydro-1H-benz[de]isoquinoline-1,3-dione with (R)-6-amino-2-(1-azabicyclo[2.2.2.]oct-3-yl)-2,3-dihydro-1H-benz[de]isoquinoline-1,3-dione, gave (R)-6-amino-2-(1-azabicyclo[2.2.2.]oct-3-yl)-5-chloro-2,3-dihydro-1H-benz[de]isoquinoline-1,3-dione hydrochloride, m.p. 344°-347° C., $[\alpha]_D^{25}$ −42.5° (c=0.425, MeOH).

Proceeding as in Example 9, but replacing chlorine with iodine, gave (RS)-6-amino-2-(1-azabicyclo[2.2.2.]oct-3-yl)-2,3-dihydro-5-iodo-1H-benz[de]isoquinoline-1,3-dione hydroiodide, m.p. 221°-223° C., $[\alpha]_D^{25}$ −33.9° (c=0.6, DMSO).

Proceeding as in Example 9, but replacing chlorine with iodine and (RS)-6-amino-2-(1-azabicyclo[2.2.2.]oct-3-yl)-2,3-dihydro-1H-benz[de]isoquinoline-1,3-dione with (R)-6-amino-2-(1-azabicyclo[2.2.2.]oct-3-yl)-2,3-dihydro-1H-benz[de]isoquinoline-1,3-dione, gave (R)-6-amino-2-(1-azabicyclo[2.2.2.]oct-3-yl)-2,3-dihydro-5-iodo-1H-benz[de]isoquinoline-1,3-dione hydrochloride, m.p. 225° C., $[\alpha]_D^{25}$ +41 ° (MeOH).

Proceeding as in Example 9 the following are prepared: 6-amino-2-(1-azabicyclo[2.2.2]oct-4-yl)-5-chloro-2,3-dihydro-1H-benz[de]isoquinoline-1,3-dione; 6-amino-5-chloro-2,3-dihydro-2-(endo-9-methyl-9-azabicyclo[3.3.1]non-3-yl)-1H-benz[de]isoquinoline-1,3-dione; 6-amino-5-chloro-2,3-dihydro-2-(exo-9-methyl-9-azabicyclo[3.3.1]non-3-yl)-1H-benz[de]isoquinoline-1,3-dione; 6-amino-5-chloro-2,3-dihydro-2-(endo-8-methyl-8-azabicyclo[3.2.1]oct-3-yl)-1H-benz[de]isoquinoline-1,3-dione; 6-amino-5-chloro-2,3-dihydro-2-(exo-8-methyl-8-azabicyclo[3.2.1]oct-3-yl)-1H-benz[de]isoquinoline-1,3-dione; (S)-6-amino-2-(endo-1-azabicyclo[3.3.1]-non-4-yl)-5-chloro-2,3-dihydro-1H-benz[de]isoquinoline-1,3-dione; (R)-6-amino-2-(endo-1-azabicyclo[3.3.1]-non-4-yl)-5-chloro-2,3-dihydro-1H-benz[de]isoquinoline-1,3-dione; (RS)-6-amino-2-(endo-1-azabicyclo[3.3.1]non-4-yl)-5-chloro-2,3-dihydro-1H-benz[de]isoquinoline-1,3-dione; (S)-6-amino-2-(exo-1-azabicyclo[3.3.1]non-4-yl)-5-chloro-2,3-dihydro-1H-benz[de]isoquinoline-1,3-dione; (R)-6-amino-2-(exo-1-azabicyclo[3.3.1]non-4-yl)-5-chloro-2,3-dihydro-1H-benz[de]isoquinoline-1,3-dione; (RS)-6-amino-2-(exo-1-azabicyclo[3.3.1]non-4-yl)-5-chloro-2,3-dihydro-1H-benz[de]isoquinoline-1,3-dione; 6-amino-2-(1-azabicyclo[2.2.2]oct-4-yl)-2,3-dihydro-5-iodo-1H-benz[de]isoquinoline-1,3-dione; 6-amino-2,3-dihydro-5-iodo-2-(endo-9-methyl-9-azabicyclo[3.3.1]non-3-yl)-1H-benz[de]isoquinoline-1,3-dione; 6-amino-2,3-dihydro-5-iodo-2-(exo-9-methyl-9-azabicyclo[3.3.1]non-3-yl)-1H-benz[de]isoquinoline-1,3-dione; 6-amino-2,3-dihydro-5-iodo-2-(endo-8-methyl-8-azabicyclo[3.2.1]oct-3-yl)-1H-benz[de]isoquinoline-1,3-dione; 6-amino-2,3-dihydro-5-iodo-2-(exo-8-methyl-8-azabicyclo[3.2.1]oct-3-yl)-1H-benz[de]isoquinoline-1,3-dione; 6-amino-2-(endo-1-azabicyclo[3.3.1]non-4-yl)-2,3-dihydro-5-iodo-1H-benz[de]isoquinoline-1,3-dione; 6-amino-2-(exo-1-azabicyclo[3.3.1]non-4-yl)-2,3-dihydro-5-iodo-1H-benz[de]isoquinoline-1,3-dione; 6-amino-2-(1-azabicyclo[2.2.2]oct-4-yl)-5-bromo-2,3-dihydro-1H-benz[de]isoquinoline-1,3-dione; 6-amino-5-bromo-2,3-dihydro-2-(endo-9-methyl-9-azabicyclo[3.3.1]non-3-yl)-1H-benz[de]isoquinoline-1,3-dione; 6-amino-5-bromo-2,3-dihydro-2-(exo-9-methyl-9-azabicyclo[3.3.1]non-3-yl)-1H-benz[de]isoquinoline-1,3-dione; 6-amino-5-bromo-2,3-dihydro-2-(endo-8-methyl-8-azabicyclo[3.2.1]oct-3-yl)-1H-benz[de]isoquinoline-1,3-dione; 6-amino-5-bromo-2,3-dihydro-2-(exo-8-methyl-8-azabicyclo[3.2.1]oct-3-yl)-1H-benz[de]isoquinoline-1,3-dione; 6-amino-2-(endo-1-azabicyclo[3.3.1]non-4-yl)-5-bromo-2,3-dihydro-1H-benz[de]isoquinoline-1,3-dione; and 6-amino-2-(exo-1-azabicyclo[3.3.1]non-4-yl)-5-bromo-2,3-dihydro-1H-benz[de]isoquinoline-1,3-dione.

EXAMPLE 10

5-chloro-2,3-dihydro-6-methylamino-2-(1-methylpiperidin-4-yl)-1H-benz[de]isoquinoline-1,3-dione The following is the preparation of a compound of Formula I via Scheme I in which
p is 0;
Z is C=O;
X is methylamino at the 6-position;
Y is chloro at the 5-position; and
R$^1$ is 1-methylpiperidin-4-yl.

A slurry of N-chlorosuccinimide (0.255 g; 1.90 mmol) and 2,3-dihydro-6-methylamino-2-(1-methylpiperidin-4-yl)-1H-benz[de]isoquinoline-1,3-dione (0.65 g; 1.80 mmol), prepared as in Example 5, in N,N-dimethylformamide (12 mL) was stirred approximately 72 hours. The solvent was removed and acetone (approximately 25 mL) was added to the residue. The acetone mixture was heated to boiling and then stirred for 1 hour at room temperature. The solid was collected from the mixture, stirred again in acetone, and recollected. Drying under vacuum gave 5-chloro-2,3-dihydro-6-methylamino-2-(1-methylpiperidin-4-yl)-1H-benz[de]isoquinoline-1,3-dione (0.65 g; 1.65 mmol), m.p. 298°-302° C.

Formation of the hydrochloride salt from ethanol containing hydrogen chloride gave 5-chloro-2,3-dihydro-6-methylamino-2-(1-methylpiperidin-4-yl)-1H-benz[de]isoquinoline-1,3-dione hydrochloride, m.p. >320° C.

Proceeding as in Example 10, but replacing 2,3-dihydro-6-methylamino-2-(1-methylpiperidin-4-yl)-1H-benz[de]isoquinoline-1,3-dione with 6-amino-2,3-dihydro-2-(piperidin-4-yl)-1H-benz[de]isoquinoline-1,3-dione gave 6-amino-5-chloro-2,3-dihydro-2-(piperidin-4-yl)-1H-benz[de]isoquinoline-1,3-dione hydrochloride, m.p. 336°-338° C.

Proceeding as in Example 10, but replacing 2,3-dihydro-6-methylamino-2-(1-methylpiperidin-4-yl)-1H-benz[de]isoquinoline-1,3-dione with 6-amino-2,3-dihydro-2-(1-methylpiperidin-4-yl)-1H-benz[de]isoquinoline-1,3-dione gave 6-amino-5-chloro-2,3-dihydro-2-(1-methylpiperidin-4-yl)-1H-benz[de]isoquinoline-1,3-dione hydrochloride, m.p. 352-354° C.

Proceeding as in Example 10, but replacing 2,3-dihydro-6-methylamino-2-(1-methylpiperidin-4-yl)-1H-benz[de]isoquinoline-1,3-dione with 6-amino-2-(1-benzylpiperidin-4-yl)-2,3-dihydro-1H-benz[de]isoquinoline-1,3-dione gave 6-amino-2-(1-benzylpiperidin-4-yl)-5-chloro-2,3-dihydro-1H-benz[de]isoquinoline-1,3-dione hydrochloride, m.p. >210° C.

Proceeding as in Example 10, but replacing 2,3-dihydro-6-methylamino-2-(1-methylpiperidin-4-yl)-1H-benz[de]isoquinoline-1,3-dione with 6-amino-2-(1-(3-(4-fluorophenoxy)propyl)piperidin-4-yl)-2,3-dihydro-1H-benz[de]isoquinoline-1,3-dione gave 6-amino-5-chloro-2-(1-(3-(4-fluorophenoxy)propyl)-piperidin-4-yl)-2,3-dihydro-1H-benz[de]isoquinoline-1,3-dione hydrochloride, m.p. >170° C.

Proceeding as in Example 10, but replacing 2,3-dihydro-6-methylamino-2-(1-methylpiperidin-4-yl)-1H-benz[de]isoquinoline-1,3-dione with 6-amino-2,3-dihydro-2-(2,2,6,6-tetramethylpiperidin-4-yl)-1H-benz[de]isoquinoline-1,3-dione gave 6-amino-5-chloro-2,3-dihydro-2-(2,2,6,6-tetramethyl-piperidin-4-yl)-1H-benz[de]isoquinoline-1,3-dione hydrochloride, m.p. >280° C.

Proceeding as in Example 10, the following are prepared: (S)-6-amino-5-chloro-2,3-dihydro-2-(methyl-piperidin-3-yl)-1H-benz[de]isoquinoline-1,3-dione; (R)-6-amino-5-chloro-2,3-dihydro-2-(methyl-piperidin-3-yl)-1H-benz[de]isoquinoline-1,3-dione; and (RS)-6-amino-5-chloro-2,3-dihydro-2-(methyl-piperidin-3-yl)-1H-benz[de]isoquinoline-1,3-dione.

EXAMPLE 11

6-amino-5-chloro-2-(1-ethylpiperidin-4-yl)-2,3-dihydro-1H-benz[de]isoquinoline-1,3-dione The following is the preparation of a compound of Formula I via Scheme I in which
p is 0;
Z is C=O;
X is amino at the 6-position;
Y is chloro at the 5-position; and
R$^1$ is 1-ethylpiperidin-4-yl.

To a solution of 6-amino-5-chloro-2,3-dihydro-2-(piperidin-4-yl)-1H-benz[de]isoquinoline-1,3-dione hydrochloride (0.9 g; 2.46 mmol), prepared as in Example 10, in methanol (30 mL) and water (5 mL), was added acetaldehyde (2 mL) and sodium cyanoborohydride (approximately 0.5 g) and the reaction mixture stirred for two hours. Additional sodium cyanoborohydride (0.4 g) was added and the mixture stirred for an additional 2 hours. The solution was concentrated to a small volume, acidified with concentrated hydrochloric acid, and then digested for 16 hours. Solid potassium carbonate was added and the solution was extracted twice with methylene chloride. The extracts were combined, dried over potassium carbonate, and concentrated. Purification by column chromatography (silica gel; 3% methanol in CH$_2$Cl$_2$ and approximately 1% NH$_4$OH) gave 6-amino-5-chloro-2-(1-ethylpiperidin-4-yl)-2,3-dihydro-1H-benz[de]isoquinoline-1,3-dione (0.6 g; 1.68 mmol).

Formation of the hydrochloride salt from ethanol containing hydrogen chloride gave 6-amino-5-chloro-2-(1-ethylpiperidin-4-yl)-2,3-dihydro-1H-benz[de]isoquinoline-1,3-dione hydrochloride (0.5 g; 1.27 mmol).

Proceeding as in Example 11, but replacing acetaldehyde with acetone gave 6-amino-5-chloro-2,3-dihydro-2-(1-isopropyl-piperidin-4-yl)-1H-benz[de]isoquinoline-1,3-dione hydrochloride, m.p. >300° C.

EXAMPLE 12

6-amino-5-chloro-2,3-dihydro-2-(1-prop-2-enylpiperidin-4-yl)-1H-benz[de]isoquinoline-1,3-dione The following is the preparation of a compound of Formula I via Scheme I in which
p is 0;
Z is C=O;
X is amino at the 6-position;
Y is chloro at the 5-position; and
R$^1$ is 1-prop-2-enylpiperidin-4-yl.

To a stirred solution of 6-amino-5-chloro-2,3-dihydro-2-(piperidin-4-yl)-1H-benz[de]isoquinoline-1,3-dione hydrochloride (0.5 g; 1.37 mmol), prepared as in Example 10, and triethylamine (0.3 g; 3.0 mmol) in N,N-dimethylformamide (10 mL), was added allyl bromide (0.17 g; 1.4 mmol) in N,N-dimethylformamide (approximately 2 mL). The reaction mixture was stirred for 1.5 hours and the solvent removed. The residue was stirred with ammonium hydroxide and methylene chloride (50 mL). The aqueous layer was further extracted with methylene chloride (2×50 mL) and purification of the combined methylene chloride layers by column chromatography (silica gel; 3% methanol in CH$_2$Cl$_2$ and approximately 1% NH$_4$OH) gave 6-amino-5-chloro-2,3-dihydro-2-(1-prop-2-enylpiperidin-4-yl)-1H-benz[de]isoquinoline-1,3-dione (0.1 g; 0.27 mmol), m.p. 279°-281° C.

Formation of the hydrochloride salt from ethanol containing hydrogen chloride gave 6-amino-5-chloro-2,3-dihydro-2-(1-prop-2-enylpiperidin-4-yl)-1H-benz[de]isoquinoline-1,3-dione (0.11 g; 0.27 mmol), m.p. 291°-230° C. Anal.: Calcd. for C$_{20}$H$_{21}$N$_3$O$_2$Cl$_2$.0.5 H$_2$O: C, 57.84; H, 5.34; N, 10.12. Found: C, 57.68; H, 5.29; N, 10.04.

Proceeding as in Example 12, but replacing allyl bromide with 1-bromoethylbenzene gave 2,3-dihydro-6-nitro-2-(1-phenylethylpiperidin-4-yl)-1H-benz[de]isoquinoline-1,3-dione hydrochloride, m.p. >200° C.

EXAMPLE 13

(S)-2-(1-azabicyclo[2.2.2]oct-3-yl-2,3-dihydro-1H-benz[de]isoquinoline-3-one

The following is the preparation of a compound of Formula I via Scheme I in which
P is 0;
Z is CH$_2$;
X and Y are hydrogen; and
R$^1$ is 1-azabicyclo[2.2.2]oct-3-yl.

(S)-2-(1-azabicyclo[2.2.2]oct-2,3-dihydro-1H-benz[de]isoquinoline-1,3-dione (1.1 g; 3.5 mmol), prepared as in Example 2, was added to a solution of NaBH$_4$ (1.3 g; 34.0 mmol) in ethanol (110 mL) and water (10 mL) and the reaction mixture stirred at ambient temperature for 5 hours. The solution was then concentrated to a small volume, treated with 10% HCl until strongly acidic and stirred for an additional 2 hours. The solution was made alkaline by addition of NaOH and then extracted with CH$_2$Cl$_2$. Purification by chromatography (silica-gel; 5% methanol in CH$_2$Cl$_2$ and approximately 1% aqueous NH$_4$OH) gave (S)-2-(1-azabicyclo[2.2.2]oct-3-yl)-2,3-dihydro-1H-benz[de]isoquinoline-3-one hydrochloride, m.p. 278°-279° C., [α]$_D^{25}$ −16.9° (c=0.48, MeOH).

Proceeding as in Example 13 the following are prepared: 6-amino-2-(1-azabicyclo[2.2.2]oct-4-yl)-5-chloro-2,3-dihydro-1H-benz[de]isoquinoline-3-one; 6-amino-5-chloro-2,3-dihydro-2-(endo-9-methyl-9-aza-bicyclo[3.3.1]non-3-yl)-1H-benz[de]isoquinoline-3-one; 6-amino-5-chloro-2,3-dihydro-2-(exo-9-methyl-9-aza-bicyclo[3.3.1]non-3-yl)-1H-benz[de]isoquinoline-3-one; 6-amino-5-chloro-2,3-dihydro-2-(endo-8-methyl-8-aza-bicyclo[3.2.1]oct-3-yl)-1H-benz[de]isoquinoline-3-one; 6-amino-5-chloro-2,3-dihydro-2-(exo-8-methyl-8-aza-bicyclo[3.2.1]oct-3-yl)-1H-benz[de]isoquinoline-3-one; 6-amino-2-(endo-1-azabicyclo[3.3.1]non-4-yl)-5-chloro-2,3-dihydro-1H-benz[de]isoquinoline-3-one; 6-amino-2-(exo-1-azabicyclo[3.3.1]non-4-yl)-5-chloro-2,3-dihydro-1H-benz[de]isoquinoline-3-one; 6-amino-2-(1-azabicyclo[2.2.2]oct-4-yl)-2,3-dihydro-5-iodo-1H-benz[de]isoquinoline-3-one; 6-amino-2,3-dihydro-5-iodo-2-(endo-9-methyl-9-aza-bicyclo[3.3.1]non-3-yl)-1H-benz[de]isoquinoline-3-one; 6-amino-2,3-dihydro-5-iodo-2-(exo-9-methyl-9-aza-bicyclo[3.3.1]non-3-yl)-1H-benz[de]isoquinoline-3-one; 6-amino-2,3-dihydro-5-iodo-2-(endo-8-methyl-8-aza-bicyclo 3.2.1]oct-3-yl)-1H-benz[de]isoquinoline-3-one; 6-amino-2,3-dihydro-5-iodo-2-(exo-8-methyl-8-aza-bicyclo[3.2.1]oct-3-yl)-1H-benz[de]isoquinoline-3-one; 6-amino-2-(endo-1-azabicyclo[3.3.1]non-4-yl)-2,3-dihydro-5-iodo-1H-benz[de]isoquinoline-3-one; 6-amino-2-(exo-1-azabicyclo[3.3.1]non-4-yl)-2,3-dihydro-5-iodo-1H-benz[de]isoquinoline-3-one; 6-amino-2-(1-azabicyclo[2.2.2]oct-4-yl)-5-bromo-2,3-dihydro-1H-benz[de]isoquinoline-3-one; 6-amino-5-bromo-2,3-dihydro-2-(endo-9-methyl-9-aza-bicyclo[3.3.1]non-3-yl)-1H-benz[de]isoquinoline-3-one; 6-amino-5-bromo-2,3-dihydro-2-(exo-9-methyl-9-aza-bicyclo[3.3.1]non-3-yl)-1H-benz[de]isoquinoline-3-one; 6-amino-5-bromo-2,3-dihydro-2-(endo-8-methyl-8-aza-bicyclo[3.2.1]oct-3-yl)-1H-benz[de]isoquinoline-3-one; 6-amino-5-bromo-2,3-dihydro-2-(exo-8-methyl-8-aza-bicyclo[3.2.1]oct-3-yl)-1H-benz[de]isoquinoline-3-one; 6-amino-2-(endo-1-azabicyclo[3.3.1]non-4-yl)-5-bromo-2,3-dihydro-1H-benz[de]isoquinoline-3-one; and 6-amino-2-(exo-1-azabicyclo[3.3.1]non-4-yl)-5-bromo-2,3-dihydro-1H-benz[de]isoquinoline-3-one.

EXAMPLE 14

The following are representative pharmaceutical formulations containing a compound of Formula I.

ORAL FORMULATION

A representative solution for oral administration contains:

| | |
|---|---|
| Compound of Formula I | 100-1000 mg |
| Citric Acid Monohydrate | 105 mg |
| Sodium Hydroxide | 18 mg |
| Flavouring | q.s. |
| Water | to 100 ml |

INTRAVENOUS FORMULATION

A representative solution for intravenous administration contains:

| | |
|---|---|
| Compound of Formula I | 10-100 mg |
| Dextrose Monohydrate isotonic | q.s. to make |
| Citric Acid Monohydrate | 1.05 mg |
| Sodium Hydroxide | 0.18 mg |
| Water for Injection | to 1.0 ml |

TABLET FORMULATION

A representative tablet form of a compound of Formula I may contain:

| | |
|---|---|
| Compound of Formula I | 1% |
| Microcrystalline cellulose | 73% |
| Stearic Acid | 25% |
| Colloidal Silica | 1% |

EXAMPLE 15

5-HT$_3$ RECEPTOR BINDING ASSAY

The following describes an in vitro assay for determining the 5-HT$_3$ receptor binding affinity of compounds of Formula I. The method is essentially that described by Kilpatrick et al., previously cited, which measures the affinity for 5-HT$_3$ receptors of the rat cerebral cortex radiolabelled with [$^1$H]quipazine.

Membranes are prepared from the cerebral cortices of rat brains homogenized in 50 mM Tris buffer (pH 7.4 at 4° C.) using a Polytron P10 tissue disrupter (setting 10, 2×10 sec bursts). The homogenate is centrifuged at 48,000×g for 12 min and the pellet obtained is washed, by resuspension and centrifugation, three times in homogenizing buffer. The tissue pellets are resuspended in the assay buffer, and are stored under liquid nitrogen until required.

The binding assays are conducted using a Tris-Krebs assay buffer of the following composition (mM): NaCl, 154; KCl, 5.4; KH$_2$PO$_4$, 1.2; CaCl$_2$. 2H$_2$O, 2.5; MgCl$_2$, 1.0; glucose, 11; Tris, 10. Assays are conducted at 25° C. at 7.4 in a final volume of 0.25 ml. Zacopride (1.0 mM) is used to define the non-specific binding (NSB). 5-HT$_3$ receptors present in rat cortical membranes are labelled using 0.3-0.7 nM [$^3$H]quipazine (specific activity 50-66 Ci/mmol; New England Nuclear) in the presence of 0.1 mM paroxetine to prevent [$^3$H]quipazine binding to 5-HT uptake sites. The rat cortex membranes are incubated with [$^3$H]quipazine in the presence of 10 different concentrations of test compound ranging from 1×10$^{-12}$ to 1×10$^{-4}$ molar. Incubations are conducted for 45 min at 25° C. and are terminated by vacuum filtration over Whatman GF/B glass fiber filters using a Brandel 48 well cell harvester. After filtration the filters are washed for 8 sec with 0.1 M NaCl. The filters are pretreated with 0.3% polyethyleneimine 18 hr prior to use in order to reduce filter binding of the radioligand. Radioactivity retained on the filters is determined by liquid scintillation counting.

The concentration of test compound producing 50% inhibition of radioligand binding, i.e., the IC$_{50}$, is determined by an iterative curve fitting procedure. Affinities are expressed as the negative logarithm of IC$_{50}$ (pIC$_{50}$). Compounds of Formula I exhibit 5-HT$_3$ receptor binding affinity, i.e., pIC$_{50}$ values greater than 6.

EXAMPLE 16

FERRET, ANTI-EMESIS ASSAY

The following describes the procedure for determining the intravenous (i.v.) effects of compounds of Formula I on cisplatin-induced emesis in ferrets.

Adult, male, castrated ferrets are allowed food and water ad libitum both prior to and throughout the testing period. Each animal is randomly chosen and anesthetized with a metofane/oxygen mixture, weighed and assigned to one of three test groups. While anesthetized an incision is made along the ventral cervical region approximately two to four centimeters in length. The jugular vein is then isolated and cannulated with a capped saline filled PE-50 polyethylene tubing. The cannula is exteriorized at the base of the skull and the incision closed with wound clips. The animals are then returned to their cages and allowed to recover from anesthesia prior to commencement of the study.

Vehicle or test compound is administered i.v. at 1.0 ml/kg and 1.0 mg/kg, respectively. Within 2.0 minutes of the administration of vehicle or test compound, cisplatin is injected i.v. at 10 mg/kg. The animals are then observed continuously for a 5 hour period and emetic responses (i.e., vomiting and/or retching) are recorded. For purposes of this example and that of Example 11, vomiting is defined as the successful evacuation of stomach contents and a single episode of retching is defined as rapid and successive efforts to vomit occurring within a one minute time period.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

Proceeding as in Example 8 but administering the test compounds by oral route, the anti-emetic effects of compounds of Formula I may be evaluated.

EXAMPLE 17

DOG, ANTI-EMESIS ASSAY

The following describes the procedure for determining the intravenous (i.v.) effects of compounds of Formula I on cisplatin-induced emesis in dogs.

Male and female dogs (6-15 kg) are fed one cup of dry dog food. One hour following feeding, cisplatin (cis-diamminedichloroplatinum) is administered i.v. at 3 mg/kg. Sixty minutes after the administration of cisplatin, either vehicle or test compound is injected i.v. at 0.1 ml/kg and 1.0 mg/kg, respectively. The dogs are then observed continuously for a 5 hour period and the emetic responses (i.e., vomiting and/or retching) are recorded.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

EXAMPLE 18

PROKINETIC ASSAY

The following describes an in vivo method of determining the prokinetic activity of the compounds of Formula I by measuring the rate of gastric emptying of test meal in rats. The method is that described by Droppleman et al., previously cited.

Test meal is prepared by slowly adding 20 grams of cellulose gum (Hercules Inc., Wilmington, Delaware) to 200 ml of cold distilled water that is being mixed in a Waring blender at approximately 20,000 rpm. Mixing continues until complete dispersion and hydration of the cellulose gum takes place (approximately 5 min). Three beef bouillon cubes are dissolved in 100 ml of warm water and then blended into the cellulose solution followed by 16 g of purified casein (Sigma Chemical Co., St. Louis, MO), 8 g of powdered confectioners sugar, 8 g of cornstarch, and 1 g of powdered charcoal. Each ingredient is added slowly and mixed thoroughly resulting in approximately 325 ml of a dark gray to black, homogenous paste. The meal is then refrigerated overnight during which time trapped air escapes. Prior to the assay the meal is removed from the refrigerator and allowed to warm to room temperature.

Mature (170 to 204 g) male Sprague-Dawley rats are deprived of food for 24 hours with water ad libitum. On the morning of the study each animal is weighed and randomly assigned to treatment groups consisting of ten animals per group. Each rat receives either vehicle, test compound or the reference standard metoclopramide by intraperitoneal injection. At 0.5 hours post injection 3.0 ml of test meal is orally administered to each rat with a 5.0 ml disposable syringe. Five test meal samples are weighed on an analytical balance and these weights are averaged to find a mean test meal weight. At 1.5 hours post injection each rat is sacrificed by carbon dioxide asphyxiation and the stomach is removed by opening the abdomen and carefully clamping and cutting the esophagus just below the pyloric sphincter. Taking care not to lose any of the its contents, each stomach is placed on a small, pre-weighed and correspondingly labeled 7 ml weigh boat and immediately weighed on an analytical balance. Each stomach is then cut open along the lesser curvature, rinsed with tap water, gently blotted dry to remove excess moisture and weighed. The amount of test meal remaining in the stomach is represented by the difference between the weight of the full stomach and the weight of the stomach empty. The difference between the amount of test meal remaining and the mean test meal weight represents the quantity of test meal that empties during the 1.5 hour post injection period.

Responses are represented as grams of meal emptied or percent change from control. Means and standard deviations of the test groups are compared to those of the reference groups. Significance is determined via Dunnett's t-test (Statistical Association Journal, Dec. 1955, 1096-112).

EXAMPLE 19

Anxiolytic Behavior Assay

The following describes an in vivo method for determining anxiolytic activity of compounds of Formula I.

Naive male C5BI/6J mice, 18-20 g, are kept in groups of 10 mice in quarters controlled for sound, temperature and humidity. Food and water are available ad libitum. The mice are kept on a 12 hour light and 12 hour dark cycle, with lights on at 6:00 a.m. and off at 6:00 p.m. All experiments begin at least 7 days after arrival on site.

The automated apparatus for detecting changes in exploration is obtained from Omni-Tech Electronics Columbus Ohio and is similar to that of Crawley and Goodwin (1980), as described in Kilfoil et al., cited previously. Briefly, the chamber consists of a plexiglass box (44×21×21 cm), divided into two chambers by a black plexiglass partition. The partition dividing the two chambers contains a 13×5 cm opening through which the mouse can easily pass. The dark chamber has clear sides and a white floor. A fluorescent tube light (40 watt) placed above the chambers provides the only illumination. The Digiscan Animal Activity Monitor System RXYZCM 16 (Omni-Tech Electronics) records the exploratory activity of the mice within the test chambers.

Prior to commencement of the study the mice are given 60 min to acclimatize to the laboratory environment. After a mouse receives an intraperitoneal (i.p.) injection of either test compound or vehicle it is returned to its home cage for a 15 min post-treatment period. The mouse is then placed in the center of the light chamber and monitored for 10 minutes.

Anxiolysis is seen as a general increase in exploratory activity in the lighted area. An increase in exploratory activity is relected by increased latency (the time for the mouse to move to the dark chamber when first placed in the center of the lighted area), increase in shuttle activity, increased or unaltered locomotor activity (number of grid lines crossed) and decreased time spent in the dark compartment.

EXAMPLE 20

Withdrawal Anxiety Assay

The following procedure describes a method to determine whether compounds of Formula I effect the anxiety that occurs after abruptly ceasing chronic treatment with drugs of abuse.

Naive male BKW mice (25-30 g) are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 12). Anxiolysis is seen as a general increase in exploratory activity in the lighted area. An increase in exploratory activity is relected by increased latency (the time for the mouse to move to the dark chamber when first placed in the center of the lighted area), increased or unaltered locomotor activity (number of grid lines crossed), increased number of rears and decreased time spent in the dark compartment.

Increased exploratory activity in the lighted area is induced by treating the mice for 14 days with ethanol (8.0 % w/v in drinking water), nicotine (0.1 mg/kg, i.p., twice daily) or cocaine ( 1.0 mg/kg, i.p., twice daily). Anxiolysis is assessed 1, 3, 7 and 14 days after commencement of the drug regime. The treatment is abruptly ceased and exploratory activity in the lighted area is determined 8, 24 and 48 hours thereafter. Vehicle or test compounds are administered during the withdrawl phase by intraperitoneal injection. Responses are represented as inhibition of the decrease in anxiolytic behavior after the ethanol, cocaine or nicotine treatment is ceased.

EXAMPLE 21

Cognitive Enhancement Assay

The following describes a model to determine the cognitive enhancing effects of compounds of Formula I.

Young adult and aged BKW mice are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 12). Mice are exposed to the two-compartment test area over a 3 day period. The young mice habituate to the test area by day 3 and spend less time exploring the lighted area, whereas exploratory activity in the lighted area remains constant through day 3 for the aged mice. Exploratory activity is seen as latency (the time for the mouse to move to the dark chamber when first placed in the center of the lighted area), locomotor activity (number of grid lines crossed), number of rears and time spent in the lighted compartment. Vehicle or test compounds are administered to the aged mice by intraperitoneal injection. Cognitive enhancing effects in the aged rats are reflected by a decrease in exploratory activity by day 3.

We claim:

1. A compound of Formula I:

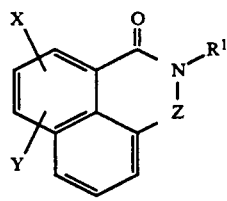

in which

Z is $CH_2$ or $C=O$;

X and Y are independently selected from hydrogen, halogen, hydroxy, lower alkoxy, lower alkyl, nitro, amino, aminocarbonyl, (lower alkyl)amino, di(-lower alkyl)amino and (lower alkanoyl)amino; and $R^1$ is a group selected from Formulae (a), (b), (c), (d) and (e):

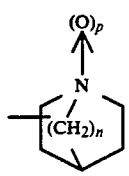

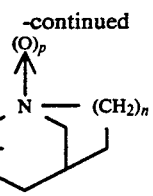

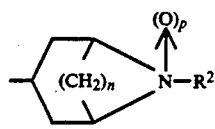

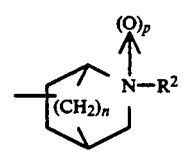

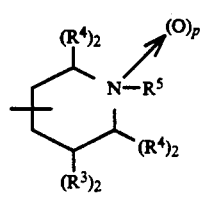

in which p is 0 or 1;

n is 1, 2 or 3;

$R^2$ is hydrogen, lower alkyl, $C_{3-8}$ cycloalkyl, $C_{3-8}$ cycloalkyl-$C_{1-2}$ alkyl, or a group $R^6$-$C_{1-2}$ alkyl in which $R^6$ is thienyl, pyrrolyl or furyl optionally substituted by one or two substituents selected from lower alkyl, lower alkoxy, trifluoromethyl or halogen, or is phenyl optionally substituted by one or two substituents selected from $C_{1-4}$ alkoxy, trifluoromethyl, halogen, nitro, carboxy, esterified carboxy, and $C_{1-4}$ alkyl optionally further substituted by hydroxy, $C_{1-4}$ alkoxy, carboxy, esterified carboxy or in vivo hydrolyzable acyloxy; each $R^3$ is independently selected from hydrogen, hydroxy, alkyl and alkoxy; each $R^4$ is independently hydrogen or alkyl; and $R^5$ is hydrogen, lower alkyl, $C_{3-8}$ cycloalkyl, $C_{3-8}$ cycloalkyl-$C_{1-2}$ alkyl, alkenyl, alkynyl or a group $R^7$-$C_{1-3}$ alkyl in which $R^7$ is phenyl or phenoxy optionally substituted by one or two substituents selected from $C_{1-4}$ alkoxy, trifluoromethyl, halogen, nitro, carboxy, esterified carboxy, and $C_{1-4}$ alkyl optionally further substituted by hydroxy, $C_{1-4}$ alkoxy, carboxy, esterified carboxy or in vivo hydrolyzable acyloxy; and the pharmaceutically acceptable salts, individual isomers, and mixtures of isomers thereof.

2. A compound of claim 1 in which X and Y are independently selected from hydrogen, halogen, amino, nitro, aminocarbonyl, (lower alkyl)amino and di(lower alkyl)amino and $R^2$ is lower alkyl.

3. A compound of claim 2 in which $R^2$ is methyl and $R^1$ is a group selected from
1-azabicyclo[2.2.2]oct-3-yl;
1-azabicyclo[2.2.2]oct-4-yl;
1-methylpiperidin-4-yl;
endo-9-methyl-9-azabicyclo[3.3.1]non-3-yl;
exo-9-methyl-9-azabicyclo[3.3.1]non-3-yl;
endo-8-methyl-8-azabicyclo[3.2.1]oct-3-yl;
exo-8-methyl-8-azabicyclo[3.2.1]oct-3-yl;

endo-1-azabicyclo[3.3.1]non-4-yl; and
exo-1-azabicyclo[3.3.1]non-4-yl.

4. A compound of claim 3 in which Z is C=0.

5. The compound of claim 4 in which X is amino in the 6-position, Y is hydrogen and $R^1$ is 1-azabicyclo[2.2.2]oct-3-yl, namely 6-amino-2-(1-azabicyclo[2.2.2]oct-3-yl)-2,3-dihydro-1H-benz[de]isoquinoline-1,3-dione or a pharmaceutically acceptable salt thereof.

6. The compound of claim 5 which is (S)-6-amino-2-(1-azabicyclo[2.2.2]oct-3-yl)-2,3-dihydro-1H-benz[de]isoquinoline-1,3-dione or a pharmaceutically acceptable salt thereof.

7. The compound of claim 6 which is (S)-6-amino-2-(I-azabicyclo[2.2.2]oct-3-yl)-2,3-dihydro--benz[de]isoquinoline-1,3-dione hydrochloride.

8. The compound of claim 5 which is (R)-6-amino-2-(1-azabicyclo[2.2.2]oct-3-yl)-2,3-dihydro-1H-benz[de]isoquinoline-1,3-dione or a pharmaceutically acceptable salt thereof.

9. The compound of claim 8 which is (R)-6-amino-2-(1-azabicyclo[2.2.2]oct-3-yl)-2,3-dihydro-1H-benz[de]isoquinoline- 13-dione hydrochloride.

10. The compound of claim 4 in which X is amino at the 6-position, Y is nitro at the 5-position and $R^1$ is 1-azabicyclo[2.2.2]oct-3-yl, namely 6-amino-2-(1-azabicyclo[2.2.2]oct-3-yl)-2,3-dihydro-5-nitro-1H-benz[de]isoquinoline-1,3-dione or a pharmaceutically acceptable salt thereof.

11. The compound of claim 10 which is (S)-6-amino-2-(1-azabicyclo[2.2.2]oct-3-yl)-2,3-dihydro-5-nitro- 1H-benz [de]isoquinoline-1,3-dione or a pharmaceutically acceptable salt thereof.

12. The compound of claim 11 which is (S)-6-amino-2-(11-azabicyclo[2.2.2]oct-3-yl)-2,3-dihydro-5-nitro-1H-benz[de]isoquinoline-1,3-dione hydrochloride.

13. The compound of claim 10 which is (R)-6-amino-2-(1-azabicyclo[2.2.2]oct-3-yl)-2,3-dihydro-5-nitro-1H-benz[de ]isoquinoline-1,3-dione or a pharmaceutically acceptable salt thereof.

14. The compound of claim 13 which is (R)-6-amino-2-(11-azabicyclo[2.2.2]oct-3-yl)-2,3-dihydro-5-nitro-1H-benz[de]isoquinoline-1,3-dione hydrochloride.

15. The compound of claim 4 in which X is amino at the 6-position, Y is iodo at the 5-position and $R^1$ is 1-azabicyclo[2.2.2]oct-3-yl, namely 6-amino-2-(11-azabicyclo[2.2.2]oct-3-yl)-2,3-dihydro-5-iodo-1H-benz[de]isoquinoline-1,3-dione or a pharmaceutically acceptable salt thereof.

16. The compound of claim 15 which is (S)-6-amino-2-(11-azabicyclo[2.2.2]oct-3-yl)-2,3-dihydro-5-iodo-1H-benz[de]isoquinoline- 13-dione or a pharmaceutically acceptable salt thereof.

17. The compound of claim 16 which is (S)-6-amino-2-(11-azabicyclo[2.2.2]oct-3-yl)-2,3-dihydro-5-iodo-1H-benz[de]isoquinoline-1,3-dione hydrochloride.

18. The compound of claim 15 which is (R)-6-amino-2-(11-azabicyclo[2.2.2]oct-3-yl)-2,3-dihydro-5-iodo-1H-benz[de]isoquinoline-1,3-dione or a pharmaceutically acceptable salt thereof.

19. The compound of claim 18 which is (R)-6-amino-2-(11-azabicyclo[2.2.2]oct-3-yl)-2,3-dihydro-5-iodo-1H-benz[de]isoquinoline-1,3-dione hydrochloride.

20. The compound of claim 4 in which X is amino at the 6-position, Y is chloro at the 5-position and $R^1$ is 1-azabicyclo[2.2.2]oct-3-yl, namely 6-amino-2-(1-azabicyclo[2.2.2]oct-3-yl)-5-chloro-2,3-dihydro- 1H-benz[de]isoquinoline-1,3-dione or a pharmaceutically acceptable salt thereof.

21. The compound of claim 20 which is (S)-6-amino-2-(1-azabicyclo[2.2.2]oct-3-yl)-5-chloro-2,3-dihydro-1H-benz[de]isoquinoline-1,3-dione or a pharmaceutically acceptable salt thereof.

22. The compound of claim 21 which is (S)-6-amino-2-(1-azabicyclo[2.2.2]oct-3-yl)-5-chloro-2,3-dihydro-1H-benz[de]isoquinoline-1,3-dione hydrochloride.

23. The compound of claim 20 which is (R)-6-amino-2-(1-azabicyclo[2.2.2]oct-3-yl)-5-chloro-2,3-dihydro-1H-benz[de]isoquinoline-1,3-dione or a pharmaceutically acceptable salt thereof.

24. The compound of claim 23 which is (R)-6-amino-2-( 11-azabicyclo[2.2.2]oct-3-yl)-5-chloro-2,3-dihydro-1H-benz[de]isoquinoline-1,3-dione hydrochloride.

25. The compound of claim 4 in which X is amino at the 6-position, Y is chloro at the 5-position and $R^1$ is -methyl-91-azabicyclo[3.3.1]non-3-yl, namely -amino-5-chloro-2,3-dihydro-2-(9-methyl-91-azabicyclo[3.3.1]-non-3-yl)-H-benz[de]isoquinoline- 13-dione or a pharmaceutically acceptable salt thereof.

26. The compound of claim 25 which is -amino-5-chloro-2,3-dihydro-1H-(endo-9-methyl-91-azabicyclo[3.3.1]non-3-yl)-H-benz[de]isoquinoline-1,3-dione or a pharmaceutically acceptable salt thereof.

27. The compound of claim 28 which is -amino-5-chloro-2,3-dihydro-2-(endo-9-methyl-91-azabicyclo[3.3.1]non-3-yl)-1H-benz[de]isoquinoline-1,3-dione hydrochloride.

28. The compound of claim 25 which is -amino-5-chloro-2,3-dihydro-2-(exo-9-methyl-91-azabicyclo[3.3.1]non-3-yl)-H-benz[de]isoquinoline-1,3-dione or a pharmaceutically acceptable salt thereof.

29. The compound of claim 28 which is 6-amino-5-chloro-2,3-dihydro-2-(exo-9-methyl-91-azabicyclo[3.3.1]non-3-yl)-H-benz[de]isoquinoline-1,3-dione hydrochloride.

30. The compound of claim 4 in which X is amino at the 6-position, Y is chloro at the 5-position, and $R^1$ is 8-methyl-81-azabicyclo[3.2.1]oct-3-yl, namely 6H-amino-5-chloro-2,3-dihydro-2-(8-methyl-81-azabicyclo[3.2.1]oct-3-yl)-1H-benz[de]isoquinoline-1,3-dione or a pharmaceutically acceptable salt thereof.

31. The compound of claim 30 which is -amino-5-chloro-2,3-dihydro-2-(endo-8-methyl-81-azabicyclo[3.2.1]oct-3-yl)-1H-benz[de]isoquinoline-1,3-dione or a pharmaceutically acceptable salt thereof.

32. The compound of claim 31 which is -amino-5-chloro-2,3-dihydro-2-(endo-8-methyl-81-azabicyclo[3.2.1]oct-3-yl)-1H-benz[de]isoquinoline-1,3-dione hydrochloride.

33. The compound of claim 30 which is 6-amino-5-chloro-2,3-dihydro-2-(exo-8-methyl-81-azabicyclo[3.2.1]oct-3-yl)-1H-benz[de]isoquinoline-1,3-dione or a pharmaceutically acceptable salt thereof.

34. The compound of claim 33 which is -amino-5-chloro-2,3-dihydro-2-(exo-8-methyl-81-azabicyclo[3.2.1]oct-3-yl)-1H-benz[de]isoquinoline-1,3-dione hydrochloride.

35. The compound of claim 4 in which X is amino at the 6-position, Y is chloro at the 5-position, and $R^1$ is 1-azabicyclo[3.3.1]non-4-yl)5-chloro-2,3-dihydro-1H-benz[de]isoquinoline-1,3-dione or a pharmaceutically acceptable salt thereof.

36. The compound of claim 35 which is 6-amino-2-(endo-1-azabicyclo[3.3.1]non-4-yl)-5-chloro-2,3-dihydro-1H-benz[de]isoquinoline-1,3-dione or a pharmaceutically acceptable salt thereof.

37. The compound of claim 36 which is (S)-6-amino-2-2-(endo-1-azabicyclo[3.3.1]non-4-yl)-5-chloro-2,3-dihydro-1H-benz[de]isoquinoline-1,3-dione or a pharmaceutically acceptable salt thereof.

38. The compound of claim 37 which is (S)-6-amino-2-(endo-1-azabicyclo[3.3.1]non-4-yl)-5-chloro-2,3-dihydro-1H-benz[de]isoquinoline-1,3-dione hydrochloride.

39. The compound of claim 36 which is (R)-6-amino-2-(endo-1-azabicyclo[3.3.1]non-4-yl)-5-chloro-2,3-dihydro-1H-benz[de]isoquinoline-1,3-dione or a pharmaceutically acceptable salt thereof.

40. The compound of claim 39 which is (R)-6-amino-2-(endo-1-azabicyclo[3.3.1]non-4-yl)-5-chloro-2,3-dihydro-1H-benz[de]isoquinoline-1,3- dione hydrochloride.

41. The compound of claim 35 which is 6-amino-2-(exo-1-azabicyclo[3.3.1]non-4-yl)-5-chloro-2,3-dihydro-1H-benz[de]isoquinoline-1,3-dione or a pharmaceutically acceptable salt thereof.

42. The compound of claim 4 which is (S)-6-amino-2-(exo-1-azabicyclo[3.3.1]non-4-yl)-5-chloro-2,3-dihydro-1H-benz[de]isoquinoline-1,3-dione or a pharmaceutically acceptable salt thereof.

43. The compound of claim 42 which is (S)-6-amino-2-(exo-11-azabicyclo[3.3.1]non-4-yl)-5-chloro-2,3-dihydro-1H-benz[de]isoquinoline-1,3-dione hydrochloride.

44. The compound of claim 4 which is (R)-6-amino-2-(exo- 11-azabicyclo[3.3.1]non-4-yl)-5-chloro-2,3-dihydro- 1H-benz[de]isoquinoline-1,3-dione or a pharmaceutically acceptable salt thereof.

45. The compound of claim 44 which is (R)-6-amino-2-(exo-11-azabicyclo[3.3.1]non-4-yl)-5-chloro-2,3-dihydro-1H-benz[de]isoquinoline-1,3-dione hydrochloride.

46. The compound of claim 4 in which X is amino at the 6-position, Y is chloro at the 5-position, and $R^1$ is 11-azabicyclo[2.2.2]oct-4-yl, namely 6-amino-2-(11-azabicyclo[2.2.2]oct-4-yl)-5-chloro-2,3-dihydro-1H-benz[de]isoquinoline-1,3-dione or a pharmaceutically acceptable salt thereof.

47. The compound of claim 46 which is 6-amino-2-(11-azabicyclo[2.2.2]oct-4-yl)-5-chloro-2,3-dihydro-1H-benz[de]isoquinoline-1,3-dione hydrochloride.

48. The compound of claim 4 in which X is amino at the 6-position, y is chloro at the 5-position, and $R^1$ is 1-methylpiperidin-4-yl, namely 6-amino-5-chloro-2,3-dihydro-2-(1-methylpiperidine-4-yl)-1H-benz-[de]isoquinoline-1,3-dione or a pharmaceutically acceptable salt thereof.

49. The compound of claim 48 which is 6-amino-5-chloro-2,3-dihydro-2-(1-methylpeperidin-4-yl)-1H-benz[de]isoquinoline-1,3-dione hydrochloride.

50. A pharmaceutical composition for treating a condition chosen from emesis, a gastrointestinal disorder treatable with prokinetic agents, anxiety/depressive state, and pain, which composition comprises a therapeutically effective amount of a compound of claim 1 in combination with a pharmaceutically acceptable carrier.

51. A method for treating a condition chosen from emesis, a gastrointestinal disorder treatable with prokinetic agents, anxiety/depressive state, and pain in an animal in need of such treatment, which method comprises administering a therapeutically effective amount of a compound of claim 1 to such animal.

52. A method of claim 51 in which the condition is pain.

* * * * *